United States Patent
Hirata et al.

(10) Patent No.: US 8,366,710 B2
(45) Date of Patent: Feb. 5, 2013

(54) EXTERNAL FIXATOR

(75) Inventors: Hitoshi Hirata, Nagoya (JP); Masahiro Tatebe, Nagoya (JP); Takaaki Shinohara, Nagoya (JP)

(73) Assignee: National University Corporation Nagoya University (JP)

( * ) Notice: Subject to any disclaimer, the term of this patent is extended or adjusted under 35 U.S.C. 154(b) by 586 days.

(21) Appl. No.: 12/302,438

(22) PCT Filed: May 25, 2007

(86) PCT No.: PCT/JP2007/060728
§ 371 (c)(1),
(2), (4) Date: Dec. 5, 2008

(87) PCT Pub. No.: WO2007/139031
PCT Pub. Date: Dec. 6, 2007

(65) Prior Publication Data
US 2009/0287212 A1    Nov. 19, 2009

(30) Foreign Application Priority Data

May 26, 2006  (WO) ................. PCT/JP2006/310561
Oct. 11, 2006  (WO) ................. PCT/JP2006/320293

(51) Int. Cl.
*A61B 17/00* (2006.01)
(52) U.S. Cl. .......................................... 606/57; 606/59
(58) Field of Classification Search .......... 606/264–278, 606/53–60
See application file for complete search history.

(56) References Cited

U.S. PATENT DOCUMENTS

| | | | | | |
|---|---|---|---|---|---|
| 2,346,346 | A | * | 4/1944 | Anderson | 606/56 |
| 4,127,119 | A | * | 11/1978 | Kronner | 606/56 |
| 4,554,915 | A | * | 11/1985 | Brumfield | 606/54 |
| 4,570,625 | A | * | 2/1986 | Harris et al. | 606/58 |
| 4,620,533 | A | | 11/1986 | Mears | |

(Continued)

FOREIGN PATENT DOCUMENTS

| | | |
|---|---|---|
| DE | 8901908.3 U1 | 3/1989 |
| EP | 0 314 021 A2 | 5/1989 |

(Continued)

OTHER PUBLICATIONS

Explanation of relevance of Japanese Office Action dated Dec. 16, 2008 with said Japanese Office Action.

(Continued)

*Primary Examiner* — Eduardo C Robert
*Assistant Examiner* — Steven Cotroneo
(74) *Attorney, Agent, or Firm* — Studebaker & Brackett PC; Donald R. Studebaker

(57) ABSTRACT

An external fixator for fixing bones includes a coupling member, a plurality of ball joints, each ball joint comprising a pin to be inserted into a bone, a rotary member in form of a ball, a supporting member in which a first supporting member and a first thread for supporting the ball rotatably are formed, and a tubular fastening member that contains the ball and that has openings at the opposite ends, the tubular fastening member is provided at one end with a second thread corresponding to the first thread. The tubular fastening member is provided at the other end with a second supporting portion for pushing the ball against the first supporting portion when the second screw is driven into the first thread, wherein the pins and the coupling member are fixed to the supporting member and the rotary member.

18 Claims, 13 Drawing Sheets

U.S. PATENT DOCUMENTS

| | | | |
|---|---|---|---|
| 4,621,627 A | | 11/1986 | DeBastiani et al. |
| 4,895,141 A | * | 1/1990 | Koeneman et al. ............ 606/54 |
| 4,978,348 A | * | 12/1990 | Ilizarov ............................ 606/57 |
| 5,443,464 A | * | 8/1995 | Russell et al. .................. 606/54 |
| 5,443,465 A | | 8/1995 | Pennig |
| 5,501,684 A | * | 3/1996 | Schlapfer et al. ............. 606/301 |
| 5,951,556 A | | 9/1999 | Faccioli et al. |
| 6,083,228 A | | 7/2000 | Michelson |
| 7,407,504 B2 | * | 8/2008 | Dongar et al. .................. 606/59 |
| 7,717,916 B2 | * | 5/2010 | Hajianpour ...................... 606/59 |
| 2001/0034520 A1 | * | 10/2001 | Enayati ............................ 606/59 |
| 2002/0004659 A1 | | 1/2002 | Boudard et al. |
| 2005/0261680 A1 | * | 11/2005 | Draper ............................. 606/59 |
| 2006/0036252 A1 | | 2/2006 | Baynham et al. |
| 2006/0155275 A1 | * | 7/2006 | Dongar et al. .................. 606/59 |
| 2009/0048599 A1 | * | 2/2009 | Hajianpour ...................... 606/59 |
| 2009/0187189 A1 | * | 7/2009 | Mirza et al. ..................... 606/59 |
| 2009/0228006 A1 | * | 9/2009 | Mussolin ......................... 606/59 |

FOREIGN PATENT DOCUMENTS

| | | |
|---|---|---|
| EP | 0383419 A1 | 8/1990 |
| EP | 0807419 A2 | 11/1997 |
| EP | 1083829 B1 | 3/2001 |
| EP | 1802249 A1 | 7/2007 |
| FR | 2808181 A1 | 2/2001 |
| GB | 2 157 179 A | 10/1985 |
| JP | 02215456 | 8/1990 |
| JP | 4036828 | 8/1992 |
| JP | 8501011 | 2/1996 |
| JP | 10043204 | 2/1998 |
| JP | 11182529 | 7/1999 |
| JP | 2002095675 | 4/2002 |
| JP | 3308271 | 5/2002 |
| JP | 2002534150 | 10/2002 |
| JP | 2003305049 A | 10/2003 |
| JP | 3593262 | 9/2004 |
| JP | 2004298253 | 10/2004 |
| JP | 2004350774 | 12/2004 |
| JP | 2005065748 | 3/2005 |
| JP | 2005065762 | 3/2005 |
| JP | 2006501908 | 1/2006 |
| WO | 89/05126 A1 | 6/1989 |
| WO | 9400066 | 1/1994 |
| WO | 9406363 | 3/1994 |
| WO | 9963891 | 12/1999 |
| WO | 0040163 | 7/2000 |
| WO | 2005053572 A2 | 6/2005 |
| WO | 2005104970 A1 | 11/2005 |
| WO | 2006038877 A1 | 4/2006 |

OTHER PUBLICATIONS

International Search Report for PCT/JP2006/310561, dated May 26, 2006, with attached Written Opinion.

International Search Report for PCT/JP2006/320293, dated Oct. 11, 2006 with attached Written Opinion.

Explanation of relevance of the Written Opinion of PCT/JP2007/060728, dated May 25, 2007 with said Written Opinion.

International Search Report for PCT/JP2007/060728 dated May 25, 2007.

Chinese Office Action "Notification of the First Office Action, PCT application in the national phase" dated Oct. 28, 2010; Chinese Patent Application No. 200780019410.9 with translation.

The Extended European Search Report dated Dec. 1, 2011; EP Application No./ Patent No. 07744162.4-2310/2030583 PCT/JP2007060728.

* cited by examiner (3A)    (3B)

EXTERNAL FIXATOR

TECHNICAL FIELD

The present invention relates to an external fixator that fixes broken bones.

BACKGROUND ART

An external fixator has been known as a device that resets and fixes bones during the treatment of broken bones. In general, an external fixator includes pins that are inserted into bones and members that connect the pins. The members and the pins are fixed not to move relative to each other, so that the bones are reset and fixed.

For example, in Japanese Patent No. 3740640, a plurality of pins are inserted into portions where bones are broken, and the plurality of pins are fixed at each of the portions by clamps. Further, the clamps are connected and fixed to each other by rod-like members that include ball joints at both ends thereof. Japanese Unexamined Patent Application Publication No. 10-43204 also discloses a technique where a plurality of pins are fixed by clamps and ball joints are connected to the clamps.

Furthermore, PCT Japanese Translation Patent Publication No. 2002-534150 and Japanese Unexamined Patent Application Publication No. 2005-65762 also disclose structure where a plurality of pins are fixed by clamps, and further disclose structure where rod-like members connecting the clamps are rotated relative to each other and bent.

Japanese Unexamined Patent Application Publication No. 2004-298253 discloses a technique where pins are fixed by ball joint means used as both balls of ball joints and sockets covering the balls. Japanese Patent No. 3308271 discloses a technique where a clamp is connected to an upper end of a fixing member having a tapered end and a fixing member and a combining member are connected to each other by tightening screws.

In addition, PCT Japanese Translation Patent Publication No. 8-501011, Japanese Patent No. 3308271, Japanese Unexamined Patent Application Publication No. 2005-65762, Japanese Unexamined Patent Application Publication No. 2-215456, Japanese Unexamined Patent Application Publication No. 2002-95675 also disclose various external fixators.

DISCLOSURE OF THE INVENTION

Since the insertion direction of the pin was limited in the above-mentioned external fixator, it was difficult to accurately insert the pin into the living body and to appropriately reset bones. Further, the direction of a rod-like member, which connected one pin with the other pin, was limited. Accordingly, when the external fixator was fixed, a degree of freedom was low and fixing strength was also low.

That is, according to Japanese Patent No. 3740640, when the clamps are connected to each other, a degree of freedom is improved due to a ball joint or a length variable rod-like member. However, since the pins inserted into bones are fixed by clamps, a degree of freedom is also significantly limited when the pin is inserted.

Specifically, according to Japanese Patent No. 3740640, a plurality of pins 5 having a large diameter are held by clamps 3 and a plurality of pins 6 having a small diameter are held by clamps 4. Accordingly, the plurality of pins 5 having a large diameter or plurality of pins 6 having a small diameter need to be disposed on the same plane, and a distance or an angle between the pins is limited. When the pin is inserted into the living body, it is very difficult to accurately control the insertion position of the pin and it is not possible to insert the pin into the bone again. Therefore, unless a very high degree of freedom is given to the insertion direction of the pin, it is very difficult to handle the external fixator.

Meanwhile, Japanese Unexamined Patent Application Publication No. 10-43204, PCT Japanese Translation Patent Publication No. 2002-534150, and Japanese Unexamined Patent Application Publication No. 2005-65762 are also similar. Since the insertion direction of a pin is regulated by a clamp in these techniques, a degree of freedom in the insertion direction of the pin is low and it is very difficult to handle an external fixator.

Further, according to Japanese Unexamined Patent Application Publication No. 2004-298253, since the pin is used while passing through the ball of the ball joint means, the rotation angle of a ball is limited. In addition, since the ball joint means is used as both the ball and the socket, it is not possible to change a distance between adjacent balls. Therefore, the external fixator needs to be fixed while the rotation angle of the ball and the distance between the balls are limited. As a result, the insertion direction of the pin is also significantly limited.

In addition, in any one of Japanese Patent No. 3308271 and the above-mentioned Japanese Unexamined Patent Application Publications, only one ball joint is connected to each of the pins. Accordingly, the rod-like members for connecting the ball joints could be set to only one direction, and the fixing position or direction of the external fixator was significantly limited. Further, according of the technique disclosed in FIG. 8 of Japanese Patent No. 3308271, while clamp members 2 are integrated with insertion members 35 and 51, the clamp members 2 need to be fixed to a fixing member 1. Accordingly, the directions of the clamp members 2 need to be determined in a range that can be selected at both ends of the insertion members 35 and 51, and it is not possible to separately and independently determine each of the directions of the clamp members 2. For this reason, when the external fixator is fixed, the direction of the fixing member 1 needs to be previously aligned with the direction that can be set in the clamp member 2 and the fixing position or direction of the external fixator was significantly limited.

In addition, since a conventional external fixator had structure a ball joint and a pin were fixed to both ends of a rod-like member elongated in one direction, it was difficult to increase strength against torsion that has a force component in a direction substantially orthogonal to the rod-like member.

Further, even in the external fixator disclosed in the above-mentioned prior art documents, after pins are fixed to a plurality of bones with broken bones interposed therebetween, there are the following difficulties in fixing structures including movable parts to the pins and fixing the movable parts of the structures.

A work for fixing bones by the external fixator is to fix the movable parts while the external fixator including movable parts is fixed and assembled to bones when the bones with broken bones interposed therebetween can move relative to each other. Accordingly, as for an operation using a conventional external fixator, when two operational objects, such as an affected area and an external fixator, are in an unstable state, a work for fixing structures including movable parts to a plurality of pins or a work for fixing the movable parts of the structures fixed to the pins by using screws or loosening the screws is forced to be repeated.

In the conventional structure where screws, which are members separated from a socket receiving a ball, are screwed to the socket in order to fix a ball joint, the ball joint is fixed by tightening or loosening a plurality of screws with a tool such as a wrench. Meanwhile, this kind of screws, which have been conventionally used, should be downsized to reduce the size and weight of the external fixator. If a bone to be treated is a small bone such as a bone of a palm, the screw cannot be designed to be large. Since the screw needs to be designed to be sufficiently smaller than the socket originally receiving the ball, it is not easy to handle the screw.

Further, in the external fixator where a plurality of screws, which are members separated from a socket receiving a ball, are screwed to the socket in order to fix a ball joint, a direction where a force for restricting the rotation of the ball is generated varies for every screw. Further, until all the screws are in contact with the ball, the contact points between the ball and the socket are not determined. Accordingly, the decrease range of a force required for changing an attitude of the coupling member, which connects the ball joint, with respect to the pin to a specific direction varies depending on screws to be loosened. Furthermore, when the contact points between the ball and the socket are not determined, a direction for changing an attitude where the decrease range of the force required for changing an attitude of the coupling member with respect to the pin to a specific direction becomes maximum is changed by loosening a specific screw.

For this reason, in the conventional structure where the plurality of screws, which are members separated from a socket receiving the ball, are screwed to the socket in order to fix the ball joint, the ball joint should be fixed while a work for tightening or loosening the plurality of screws is repeated. Therefore, in this kind of conventional structure, it is very difficult to fix the ball joint while adjusting the attitude of the coupling member with respect to the pin.

Further, in the external fixator where one screw, which is a member separated from a socket receiving a ball, is screwed to the socket in order to fix a ball joint, the increase range of the force for restricting an attitude of the coupling member with respect to the pin by tightening the screw varies depending on the change direction of the attitude. Accordingly, even in this structure, it is very difficult to fix the ball joint while adjusting the attitude of the coupling member with respect to the pin.

The present invention has been made in consideration of the above-mentioned problems, and an object of the present invention is to facilitate a work for fixing bones with an external fixator.

(1) An external fixator for achieving the object includes a plurality of pins that are inserted into bones, a coupling member, and a plurality of ball joints. The ball joints fix the coupling member to the pins and are connected to each other by the coupling member. Also, the ball joints each include a rotary member, at least a part of which is a ball; a supporting member where a first screw and a first supporting portion that rotatably supports the ball are formed; and a tubular-shaped fastening member that has openings at both end portions thereof and receives the ball. A second screw corresponding to the first screw is formed at one end portion of each of the fastening members. A second supporting portion, which presses the ball against the first supporting portion by screwing the second screw to the first screw, is formed at the other end portion of each of the fastening members. The pin and the coupling member are fixed to the supporting member and the rotary member.

In the external fixator having this structure, in order to fix the ball joint, the ball and the supporting member are unrotatably fixed relative to each other. Accordingly, the ball may be pressed against the second supporting portion of the supporting member by rotating the fastening member, which receives the ball, with respect to the supporting member. Screws separated from the fastening member are not required. In the external fixator according to the present invention, the ball joint is fixed by rotating the fastening member, which receives the ball, with respect to the supporting member. Accordingly, the fastening member, which is an object to be operated to fix the ball joint, may be designed to be large, and the ball joint may be adjusted and fixed by rotating one member. Therefore, the external fixator according to the present invention facilitates a work for fixing bones.

(2) In the external fixator for achieving the object, when the second screw is screwed to the first screw, the second supporting portion may press the ball against the first supporting portion while supporting the ball at three points. When the ball is in contact with the first and second supporting portions, it is preferable that a centroid of contact points between the ball and the first and second supporting portions correspond to the center of the ball.

According to this structure, as long as the ball is in contact with the first and second supporting portions, a frictional force, which becomes a force for restricting the rotation of the ball, is independent of the rotational direction of the ball. Further, even though the ball is rotated in any direction, resistance is the same. Accordingly, in the external fixator having this structure, if only one member (fastening member) is rotated, forces required for adjusting an attitude of the coupling member with respect to the pin can be fixed while being simultaneously adjusted for the attitude change in all directions. In the external fixator having this structure, if only one member (fastening member) is rotated, forces for fixing the attitude of the coupling member with respect to the pin may be simultaneously increased for the attitude change in all directions. As a result, it is easier to fix bones by the external fixator.

(3) The external fixator for achieving the object may further include third screws each of which is screwed to one, which is provided outside, of the fastening member and the supporting member and thus presses the other provided inside, and fixes the fastening member to the supporting member so that the fastening member and the supporting member are not rotated.

If a patient moves, a twist force is applied to the ball joint from the coupling member or a pin in a direction where the second screw of the fastening member is loosened. Accordingly, a fastening force between the fastening member and the supporting member is gradually decreased. However, since the external fixator includes a third screw, it is possible to continuously maintain the fastening force between the fastening member and the supporting member.

(4) In the external fixator for achieving the object, at least one of the rotary member and the supporting member may be magnetized so as to attract the other thereof.

Even before the fastening member is screwed to the supporting member so that the ball is pressed against the first supporting portion, it is possible to temporarily fix the attitude of the coupling member with respect to the pin by a magnetic force due to this structure. Accordingly, it is easier to fix bones by the external fixator.

(5) In the external fixator for achieving the object, each of the rotary member and the supporting member may be formed of a plastic magnet.

While the bonding state of broken bones is confirmed using an X-ray, an external fixator is used in order to treat broken bones. If the external fixator is made of a material having a low X-ray transmittance, the color of the external fixator in an X-ray image is dark, and hence it is difficult to confirm the broken bones. Accordingly, each of the rotary member and the supporting member is formed of a plastic magnet, so that it is possible to obtain an external fixator that allows the pin and the coupling member to be temporarily fixed by a magnetic force and allows the broken bones to be easily confirmed.

Meanwhile, it is preferable that components excluding the rotary member and the supporting member be made of a material that contains a resin having an X-ray transmittance higher than that of metal as a base material.

(6) An external fixator for achieving the object includes a plurality of pins that are inserted into bones, a coupling member, and a plurality of ball joints that fix the coupling member to the pins and are connected to each other by the coupling member. Each of the ball joints includes a rotary member, at least a part of which is a ball; a socket including a recess in which a centroid of the ball is disposed and a screw hole that reaches the recess from outer surfaces; and a screw that is screwed to the screw hole and thus presses the ball against the recess. The pin and the coupling member are fixed to the socket and the rotary member, and at least one of the rotary member and the socket is magnetized so as to attract the other thereof.

According to the external fixator, at least one of the rotary member and the socket is magnetized so as to attract the other thereof. Accordingly, even before the screw presses the ball against the recess of the socket, it is possible to temporarily fix the pin and the coupling member by a magnetic force. Therefore, it is easy to fix bones by the external fixator.

The ball joint is formed by the combination of a ball and a socket that can be rotated with respect to the ball. The pin and the coupling member are connected to each other by the ball joint, so that it is possible to give a high degree of freedom to a relationship between the pin and the coupling member. Accordingly, for example, the size of the ball and the size of the socket may be adjusted and the operation ranges thereof are may be adjusted so that the ball joint is fixed to the pin that is inserted into the bone in an arbitrary direction and the coupling member is fixed to the ball joint regardless of the position of the ball joint to form an external fixator.

Further, the ball of the ball joint may be disposed on and fixed to the recess, and the recess may be a substantially semi-spherical recess having substantially the same diameter as the ball. The recess may be a rectangular recess, and a distance between the end face of the recess and the deepest portion of the recess may be larger than the radius of the ball. The centroid of the ball may be disposed inside (recess side) of the end face of the recess.

Furthermore, it is preferable that screws and the walls of the recess be in contact with the ball at least four points, and the centroid of the ball be disposed in a tetrahedron whose apexes are the four contact points. If this structure is employed, the ball and the socket can be fixed by any one of the plurality of screw holes or the combination thereof. Accordingly, even though the body is disposed in any direction with respect to the ball, it is possible to select a screw hole where the screw is easily tightened, to fix the ball and the socket, and to very easily fix the external fixator. When the size of the external fixator is small or when a portion to which the external fixator is to be fixed has a complicated shape, this effect is particularly significant.

(7) In the external fixator for achieving the object, each of the rotary member and the socket may be formed of a plastic magnet.

Each of the rotary member and the socket is formed of a plastic magnet, so that it is possible to obtain an external fixator that allows the pin and the coupling member to be temporarily fixed by a magnetic force and allows the broken bones to be easily confirmed.

Meanwhile, it is desirable that components excluding the rotary member and the supporting member be made of a material that contains a resin having an X-ray transmittance higher than that of metal as a base material.

(8) In the external fixator for achieving the object, any one of the rotary member and the socket of at least one ball joint may be fixed to the end of the pin, and the other thereof may be fixed to the fixed rotary member or socket.

According to this structure, since the pin does not pass through the ball of the rotary member, it is possible to rotate the rotary member without being affected by the pin and to connect the coupling member to the end of the pin (a portion opposite to the bone) with a very high degree of freedom. Further, it is possible to separately and independently determine the direction of the socket at the end of each pin. Accordingly, it is possible to determine a relationship between the socket and the coupling member regardless of the insertion direction of the pin, and to give a very high degree of freedom to the insertion direction of the pin or the direction of the coupling member.

Meanwhile, any one of the rotary member and the socket may be connected to the pin, and the rotary member is connected to the pin, the rotary member may be connected to the end of the pin. In this case, the socket is connected to a portion, which is opposite to the pin, on the outer circumference of the ball. Therefore, it is possible to determine the direction of the socket at the end of the pin with a very high degree of freedom.

Even when the socket is connected to the pin, it is possible to rotate the ball, which is received in the socket, regardless of the direction of the pin by connecting the socket to the end of the pin. Meanwhile, when the socket is connected to the pin, the socket may be connected to the pin so that the pin and the coupling member can be connected to each other by the ball joint. When the socket is connected to the pin, it is possible to appropriately adjust the direction.

(9) In addition, when the plurality of ball joints are connected to each of the pins, a ball joint is connected between one end of the pin and the other end thereof. Accordingly, as an example of preferred structure, there may be employed a structure where an insertion portion to which a pin can be inserted and fixed is formed at any one of the rotary member and the socket of the ball joint.

That is, in the external fixator for achieving the object, the ball joint may include an insertion portion, where a through hole is formed, at any one of the rotary member and the socket. The pin may be inserted into and fixed to the through hole of the insertion portion.

According to this structure, any one of the rotary member and the socket can be rotated about the pin inserted into the through hole. Therefore, after any one of the rotary member and the socket is rotated and positioned, the rotary member and the socket can be connected to each other. As a result, it is possible to connect the rotary member and the socket with a very high degree of freedom.

Meanwhile, to connect a ball joint between one end of the pin and the other end thereof, an insertion portion may be formed by forming a portion that protrudes from any one of the rotary member and the socket, and forming a through hole in the portion

(10) In the external fixator for achieving the object, the plurality of ball joints may be fixed to each of the pins.

When a plurality of ball joints are connected to one pin, the directions of the coupling members are not limited to one direction, so that it is possible to obtain an external fixator that has a very high degree of freedom in fixing. Further, if the external fixator is fixed while the coupling members are oriented in several directions, the external fixator can be fixed so as to have high strength against forces applied from various directions.

Furthermore, ball joints are connected to a plurality of pins so that one or more ball joints are connected to each of n (n is 2 or more) pins and n or more ball joints are connected in total. It is possible to give a very high degree of freedom to a relative positional relationship between the pin and the coupling member by fixing the pin and the coupling member by the ball joint. Accordingly, even though the plurality of pins are inserted into the bone in any direction, it is possible to connect the ball joints to each other by the coupling member without being affected by the directions and to fix the pins.

In addition, the limitation on a distance or angle between the pins (for example, the limitation where a plurality of pins should be inserted into a certain portion so as to parallel to each other) is removed by connecting different ball joints to a plurality of pins respectively, and the pins do not need to be disposed on the same plane. Accordingly, if the different ball joints are connected to each of the plurality of pins, it is possible to insert pins at the position and in the direction, which are required for resetting the bones, without the need to consider of the insertion angle of the pin when the external fixator is fixed. As a result, it is possible to provide a user-friendly external fixator.

(11) In the external fixator for achieving the object, the coupling member may include a plurality of connection portions that are connected to the ball joints, and the positions of the plurality of connection portions may be adjusted at least in a longitudinal direction of the coupling member.

In this structure, the position of the connection portion that connects the coupling member with the ball joint may be adjusted at least in a longitudinal direction of the coupling member. Accordingly, even though a distance between the ball joints connected to the pins has any value when the plurality of pins are inserted into the bones in arbitrary directions, it is possible to connect the coupling member and the ball joint while satisfying the distance. Therefore, it is possible to provide a user-friendly external fixator.

The coupling member can connect the ball joints, and the connection portion may be adjusted at least in the longitudinal direction of the coupling member. Accordingly, various structures may be employed the position of the connection portion may be adjusted by adjusting the length of the coupling member, the ball joints may be connected to the coupling member at a plurality of positions, and the position of the connection portion may be adjusted by forming the coupling member by a plurality of members and adjusting the angle between the connected members.

(12) The structure where the first to third rod-like members are connected by the screw mechanisms and the length can be adjusted by rotating the first rod-like member may be used as the structure of the coupling member that adjusts the position of the connection portion with respect to the ball joint.

That is, in the external fixator for achieving the object, the coupling member may include a first rod-like member and second and third rod-like members that are connected to both ends of the first rod-like member by screw mechanisms, and one of the screw mechanisms provided at the both ends may be a right-hand thread and the other thereof may be a left-hand thread.

According to this structure, while being rotated with respect to the first rod-like member in a certain rotational direction, the second rod-like member can be screwed. While being rotated with respect to the first rod-like member in a reverse rotational direction, the third rod-like member can be screwed. Accordingly, if the first rod-like member is rotated in a certain direction while the second and third rod-like members are connected to the first rod-like member, the second and third rod-like members approach each other while being rotated. If the first rod-like member is rotated in a reverse direction, the second and third rod-like members move to be separated from each other.

As a result, it is possible to adjust the entire length of the coupling member, where the first to third rod-like members are combined, by rotating the first rod-like member. Accordingly, it is possible to very easily adjust the length of the coupling member, and to adjust the positions of the connection portions between the coupling member and the ball joint by this adjustment.

Meanwhile, the length of the combined first to third rod-like members may be adjusted by the screw mechanisms. For example, the first rod-like member may be formed of a tubular member, a thread groove may be formed on the inner wall, each of the second and third rod-like members may be formed of a columnar member, and threads may be formed on the outer walls thereof. Any one of the first to third rod-like members may be formed in a tubular shape, a thread groove may be formed on any one of the rod-like members, and various combinations may be employed.

(13) In addition, the structure where coupling member is formed by connecting a plurality of rod-like members and connection angles thereof may be adjusted may be employed as the structure of the coupling member that adjusts the position of the connection portion with respect to the ball joint. For example, in the external fixator for achieving the object, the coupling member may include two rod-like members and the two rod-like members may be connected so as to be rotated on at least a plane between the ball joints that are connected to each other by the coupling member.

In this structure, if the ball joint is connected to each of the ends of the two rod-like members, it is possible to adjust the positions of the connection portions of the ball joints by rotating the two rod-like members relative to each other. Meanwhile, the two rod-like members may be formed to be rotated on at least a plane where at least the connection portions are positioned, and the connection portion may also be formed of a ball joint and the rod-like members may be formed to be rotated with a high degree of freedom.

The above-mentioned external fixator may be applied to a treatment method of resetting bones and treating broken bones. The external fixator may also be used for bones of a human body and animals. Further, the size of the external fixator is not particularly limited, but the external fixator according to the present invention has a very high degree of freedom when the pins are inserted into bones. Accordingly, the external fixator can be applied to the treatment even in the case of a complicated portion of a living body, a small bone, or complicated fracture.

BEST MODE FOR CARRYING OUT THE INVENTION

Herein, an embodiment of the present invention will be described in the following order.
(1) Schematic structure of external fixator:
(2) Structure of pin and rotary member:
(3) Structure of socket:
(4) Structure of coupling member:
(5) Other embodiments:

(1) Schematic Structure of External Fixator

Figure 1:
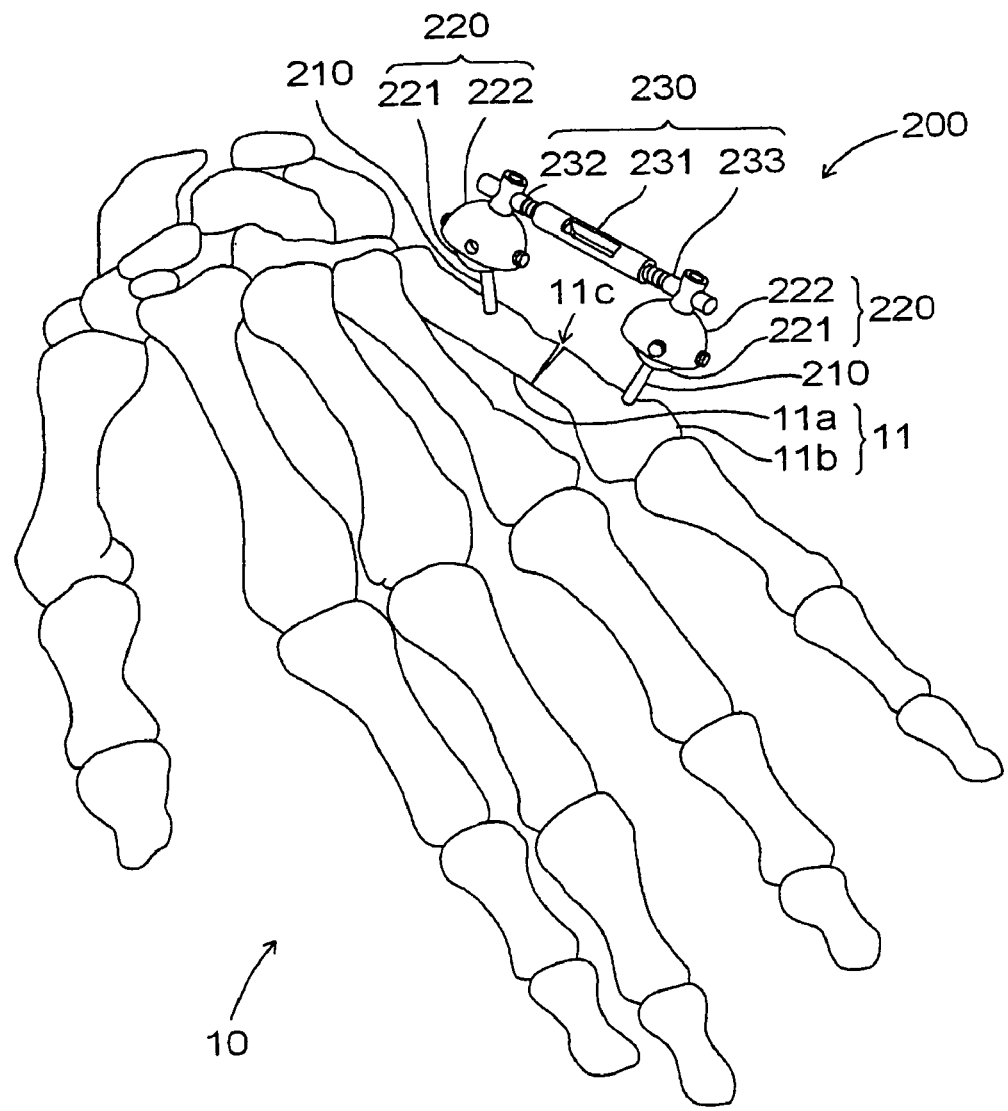
FIG. 1 is a view showing an external fixator according to an embodiment of the present invention.

FIG. 1 is a view showing an external fixator according to an embodiment of the present invention. FIG. 1 shows bones 10 of a human hand and shows that one bone 11 of the bones is broken at a portion 11c. The broken bone 11 includes a bone 11a and a bone 11b, and an external fixator 200 according to this embodiment is fixed to the bones in order to fix the bones while the bones are reset.

In FIG. 1, pins 210 are inserted into the bones in order to reset the bone 11a and the bone 11b, respectively. When a treatment is performed, the pins 210 are pierced to the skin and the pins 210 are inserted into the bones 11a and 11b. A ball joint 220 is connected to an end of each of the pins 210 opposite to the bone 11.

The ball joint 220 includes a ball 221 used as a rotary member and a socket 222. While the ball 221 is fitted to the socket 222, the direction of the socket 222 can be changed with a high degree of freedom. The socket 222 has holes in which thread grooves are formed. A hexagon socket set screw is screwed into the hole, so that the socket 222 can be fixed to the ball 221.

An insertion portion into which a coupling member 230 can be inserted is formed at each of the sockets 222, and the coupling member 230 is inserted into the insertion portion and fixed by a screw, so that it is possible to fix the coupling member 230 to the socket 222. The coupling member 230 includes a first rod-like member 231, a second rod-like member 232, and a third rod-like member 233.

The first rod-like member 231 is a substantially cylindrical member, and has a hole formed at the middle portion of an outer wall thereof and thread grooves formed on the inner walls of both ends thereof. Each of the second and third rod-like members 232 and 233 is a substantially cylindrical member, and a thread groove is formed at one end portion of each of the second and third rod-like members. One of the thread grooves formed at the both ends of the first rod-like member 231 corresponds to a right-hand thread, and the other thereof corresponds to a left-hand thread. The thread groove of the second rod-like member 232 corresponds to one of the thread grooves formed at the both ends of the first rod-like member, and the thread groove of the third rod-like member 233 corresponds to the other thereof.

Accordingly, when the second and third rod-like members 232 and 233 are rotated so as to be inserted into the first rod-like member 231, the rotational directions of the second and third rod-like members are opposite to each other. It is possible to increase or decrease a distance between the second and third rod-like members 232 and 233 by rotating the first rod-like member 231 while the second and third rod-like members 232 and 233 are inserted into the first rod-like member 231. For this reason, in this embodiment, it is possible to adjust the length of the coupling member 230 by rotating the first rod-like member 231.

In this embodiment as described above, the ball joint 220 is connected to the end of each of the pins 210, and the coupling member 230 is connected to the socket 222. Further, since the length of the coupling member 230 can be adjusted, it is possible to easily adjust the position of a connection portion between the coupling member 230 and the ball joint 220 (a portion of the coupling member 230 fixed to the insertion portion of the socket 222 by a screw in this embodiment).

Accordingly, it is possible to fix the pins 210, the ball joint 220, and the coupling member 230 with a very high degree of freedom regardless of the insertion direction of the pin 210. That is, when the pins 210 are inserted into the bones 11a and 11b, the pins 210 are pierced to the skin and the pins 210 reach the bones 11a and 11b inside the skin. Accordingly, it is not possible to insert the pins 210 while seeing the shape or state of each of the bones 11a and 11b.

Further, since the bones 11a and 11b exist in a living body and are broken, it is extremely difficult to fix the bones in the living body. Furthermore, since the bones 11a and 11b are pushed as the pins 210 are inserted into the bones, the positions or directions of the bones may be easily changed. Accordingly, it is extremely difficult to insert the pins 210 into the bones at desired positions or angles in the living body.

However, according to this embodiment, even though the pins 210 are inserted into the bones 11a and 11b at any angle, the balls 221 are connected to the ends of the pins 210 exposed to the outside of the skin. Accordingly, it is very easy to fit the sockets 222 to the balls 221 at desired angles. Meanwhile, in this case, it is possible to separately and independently determine the direction of the socket 222 with respect to each of the pins 210, and to determine a relationship between the socket 222 and the coupling member 230 regardless of the insertion direction of the pin 210. Therefore, it is possible to provide a very high degree of freedom to the insertion direction of the pin 210 or the direction of the coupling member 230.

Further, as for the coupling member 230, the second and third rod-like members 232 and 233 can be inserted into the first rod-like member 231 by a screw mechanism. Furthermore, it is possible to adjust the length of the coupling member by rotating the first rod-like member 231. Therefore, regardless of the insertion direction of the pin 210, it is possible to very easily connect to the pin 210 to the ball joint 220 and to connect the ball joint 220 to the coupling member 230.

For example, in a state where the first to third rod-like members have been connected to each other, the second rod-like member 232 and the socket 222 are temporarily fixed to each other and the third rod-like member 233 and the socket 222 are temporarily fixed to each other. Further, if the position of the connection portion is finely adjusted by adjusting the length of the coupling member 230 while one of the balls 221, which are connected to the ends of the pins 210 inserted into the bones at an arbitrary position and direction, is fitted to one socket 222, it is possible to very easily fit the other ball 221 to the other socket 222.

The balls 221 are fitted to the sockets 222, respectively, the balls 221 and the sockets 222 are fixed to each other by screws, and the coupling member 230 is fixed to the sockets 222, so that it is possible to completely fix the external fixator 200.

Meanwhile, the fixing order of the other parts except for the pins 210 is not particularly limited in this embodiment. The various fixing orders may be employed. For example, the sockets 222 are temporarily fixed to the balls 221 after the pins 210 are inserted into the bones, the second and third rod-like members 232 and 233 are inserted into the insertion portions of the sockets 222, and the first rod-like member 231 is disposed between the second and third rod-like members and connected thereto by means of a screw. Further, when the external fixator 200 is fixed, an operation for releasing the temporary fixing or an operation for strengthening the temporary fixing by tightening screws may be appropriately employed.

(2) Structure of Pin and Rotary Member

Figure 2:
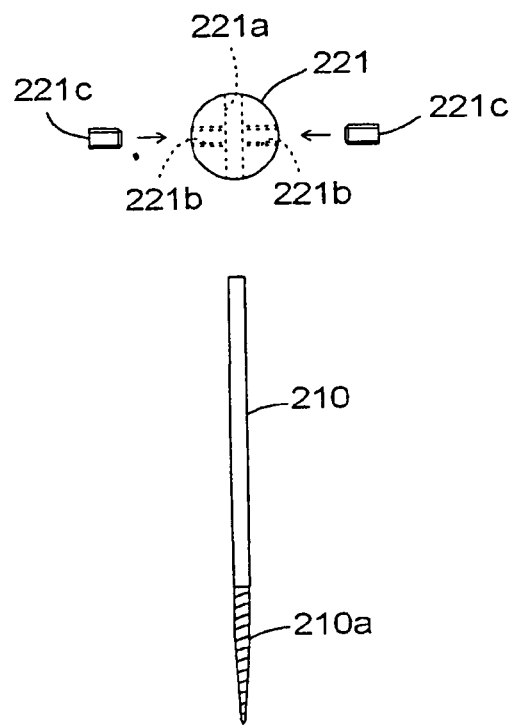
FIG. 2 is a view illustrating the structure of a pin and a ball.

Next, the structure of the pin 210 and the ball 221, which is used as the rotary member, of this embodiment will be described in detail. FIG. 2 is a view illustrating the structure of the pin 210 and the ball 221. The pin 210 is a substantially columnar member. One end portion of the pin becomes thinner toward the end thereof as shown in FIG. 2, and has a thread groove 210a.

The ball 221 is a substantially spherical body, and includes a hole 221a into which the pin 210 is inserted and screw holes 221b that are used to fix the pin 210 by screws. That is, the hole 221a is a hole passing through the center of the ball 221, and the inner diameter thereof is substantially the same as the outer diameter of the pin 210. Accordingly, it is possible to fit the pin 210 into the hole 221a.

While being fitted into the hole 221a, the pin 210 is fixed by hexagon socket set screws 221c inserted into the screw holes 221b. The ball 221 has been connected to the end of the pin 210 in this embodiment. However, the pin 210 may be fixed by screws so that the pin 210 does not pass through the ball 221. Alternatively, after the pin is fixed by screws so that the pin 210 passes through the ball 221, one end of the pin may be cut and the ball 221 may by connected to one end of the pin 210.

Anyway, the ball 221 is connected to the end of the pin 210 and the pin 210 is not allowed to pass through the ball 221. Accordingly, the entire range where the pin 210 and the socket 222 do not interfere with each other may be referred to as an operation range of the socket 222. As a result, it is possible to provide a very high degree of freedom in the direction of the socket 222.

(3) Structure of Socket

Figure 3:
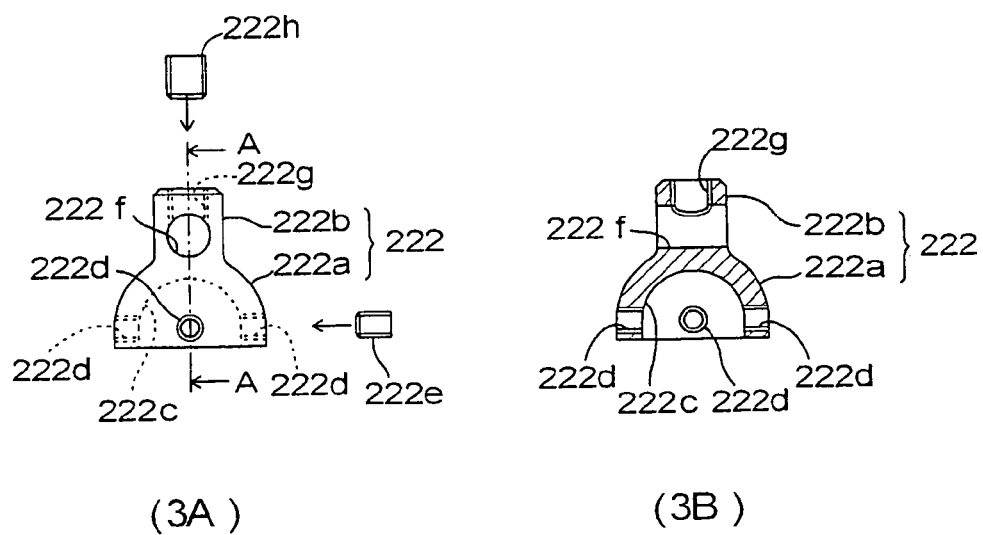
FIG. 3A is a view illustrating a socket.
FIG. 3B is a cross-sectional view taken along line A-A of FIG. 3A.

Next, the structure of the socket 222 of this embodiment will be described in detail. FIG. 3A is a view where the surface of the socket 222 being in contact with the ball 221 is shown on the lower side and the insertion portion into which the coupling member 230 is inserted is shown on the upper side. FIG. 3B is a cross-sectional view taken along line A-A of FIG. 3A. Meanwhile, the inner structure of the socket will be shown by a dotted line in FIG. 3A.

The socket 222 includes a body 222a that has a substantially semi-spherical shape, and a substantially columnar insertion portion 222b that protrudes from the body 222a. A substantially semi-spherical recess 222c is formed in the body 222a. The recess 222c is formed by cutting a semi-sphere that has substantially the same diameter as the ball 221. Accordingly, while the ball 221 is fitted to the socket 222, it is possible to adjust the direction of the socket 222 with a high degree of freedom.

In this embodiment, screw holes 222d are formed at four positions on the side surface of the body 222a. The screw holes 222d are holes that have the same diameter and are formed to reach the recess 222c formed in the body 222a from the outer wall of the body 222a. The screw holes 222d are positioned on a circumference circle of the body 222a at substantially regular intervals. Meanwhile, a plurality of screw holes 222d may be formed. The number of screw holes is not limited to four, and may be appropriately adjusted.

A hexagon socket set screw 222e can be screwed into each of the screw hole 222d, and it is possible to fix the socket 222 to the ball 221 by screwing the hexagon socket set screws 222e into one or more screw holes 222d while the ball 221 is fitted to the socket 222. Meanwhile, in this embodiment, an intersection of lines passing through axes of the screw holes 222d corresponds to the centroid position of the ball 221 when the ball 221 is in contact with the recess 222c. Accordingly, the recess 222c of this embodiment is a recess in which a centroid of the ball may be disposed.

Meanwhile, the number of the screw holes 222d to be used to fix the socket may be determined according to the strength that is required to fix the socket. Further, since four screw holes 222d have been positioned on the circumference circle of the body 222a as described above in this embodiment, the socket 222 may be fixed to the ball 221 by using arbitrary screw holes 222d. Accordingly, it is possible to select screw holes 222d where the hexagon socket set screws 222e can be screwed without interfering with a portion of a human body regardless of the direction of the socket 222, thereby very easily screwing the hexagon socket set screws.

The insertion portion 222b protrudes from the outer surface of the body 222a of the socket 222 in a direction opposite to the recess 222c, has a substantially columnar shape, and includes an insertion hole 222f that extends in a direction substantially orthogonal to an axis of the columnar shape. The inner diameter of the insertion hole 222f is substantially equal to the outer diameter of each of the second and third rod-like members 232 and 233, and the second or third rod-like member 232 or 233 can be inserted into the insertion hole 222f.

Further, a screw hole 222g, which extends from the upper end of the insertion portion to the inside of the socket 222, is formed in the insertion portion 222b. A hexagon socket set screw 222h can be screwed into the screw hole. Accordingly, it is possible to fix the coupling member 230 to the socket 222 by screwing the hexagon socket set screw 222h into the screw hole 222g while the second or third rod-like member 232 or 233 is inserted into the insertion portion 222b.

(4) Structure of Coupling Member

Figure 4:
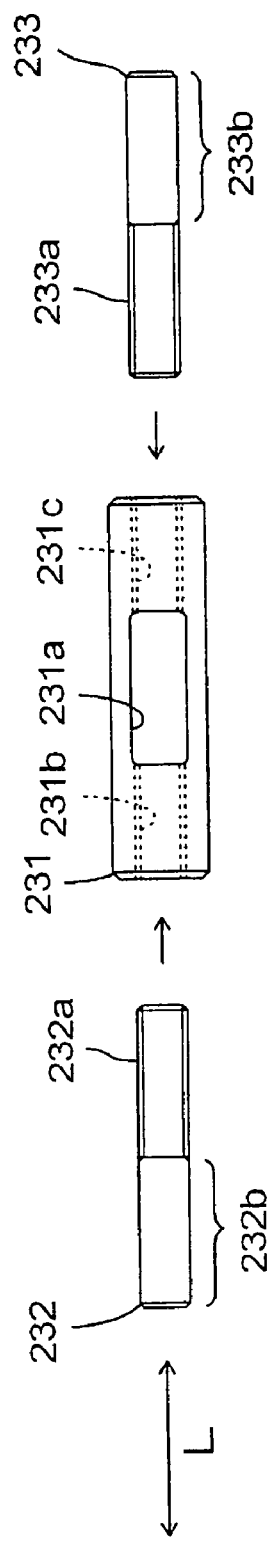
FIG. 4 is a view illustrating rod-like members.

Next, the structure of the coupling member 230 of this embodiment will be described in detail. FIG. 4 is a view illustrating the first, second, and third rod-like members 231, 232, and 233, which form the coupling member 230. The inner structure of the first rod-like member 231 will be shown by a dotted line.

The first rod-like member 231 is a substantially cylindrical member. The first rod-like member has a hole 231a formed at the middle portion thereof and thread grooves 231b and 231c formed on the inner walls of portions that are closer to the both ends thereof than the hole 231a. The direction of the thread groove 231b is opposite to that of the thread groove 231c. For example, if the thread groove 231b corresponds to a right-hand thread, the thread groove 231c corresponds to a left-hand thread.

Meanwhile, each of the second and third rod-like members 232 and 233 is a substantially columnar member, and thread grooves 232a and 233a are formed on one end portions of the second and third rod-like members, respectively. The outer diameter of each of the second and third rod-like members 232 and 233 is substantially equal to the inner diameter of the first rod-like member 231. In FIG. 4, the direction of the thread groove 232a corresponds to the thread groove 231b, and the direction of the thread groove 233a corresponds to the thread groove 231c.

Accordingly, the second rod-like member 232 may be screwed to the thread groove 231c, and the third rod-like member 233 may be screwed to the thread groove 231c. In this case, the direction of the thread groove 231b is opposite to that of the thread groove 231c as described above. Therefore, the rotational direction of the second rod-like member 232 when the second rod-like member is screwed to the first rod-like member 231 is opposite to that of the third rod-like member 233 when the third rod-like member is screwed to the first rod-like member 231.

As a result, it is possible to increase or decrease a distance between the second and third rod-like members 232 and 233 by rotating the first rod-like member 231 with respect to the second and third rod-like members 232 and 233. That is, it is possible to adjust the length of the coupling member 230 by rotating the first rod-like member 231 with respect to the second and third rod-like members 232 and 233. Meanwhile, since the length of the coupling member 230 is adjusted by the rotation of the first rod-like member 231 in this embodiment, an antislip groove and the like may be formed on the outer surface of the first rod-like member 231.

Columnar portions 232b and 233b, which are formed at portions of the second and third rod-like members 232 and 233 opposite to the thread grooves 232a and 233a, are portions that can be inserted into the above-mentioned insertion portions 222f and fixed by the hexagon socket set screws 222h. Accordingly, when the second and third rod-like members 232 and 233 are fixed to the sockets 222, it is possible to adjust the length of the coupling member 230 while the second and third rod-like members 232 and 233 are inserted into the insertion portions 222f, and to fix the second and third rod-like members by bringing the hexagon socket set screws 222h into contact with arbitrary positions on the columnar portions 232b and 233b.

That is, the positions where the hexagon socket set screws 222h are in contact with the columnar portions 232b and 233b (the positions of the connection portions) can be adjusted in a longitudinal direction of the coupling member 230 (L in FIG. 4). Accordingly, even though the pins 210 are inserted into the bone 11 in certain directions and a distance between the balls 221 connected to the pins 210 corresponds to a certain value, it is possible to adjust the length of the coupling member 230, to easily make the distance between the balls correspond to the length of the coupling member, and to very easily fix the external fixator 200.

Meanwhile, since the length of the coupling member 230 can be adjusted in this embodiment, it is possible to connect the sockets 222 after adjusting the length of the coupling member 230 as short as possible. Therefore, it is possible to make the external fixator 200 as small as possible, and to suppress the influence on the action of a user of the external fixator 200.

Further, the columnar portions 232b and 233b have been formed at the second and third rod-like members 232 and 233 so as to be in contact with the hexagon socket set screws 222h. However, it is possible to fix the second and third rod-like members by bringing the hexagon socket set screws 222h into contact with the thread grooves 232a and 233a in order to fix the second and third rod-like members without stripping the thread grooves 232a and 233a.

(5) Other Embodiments

Figure 5:
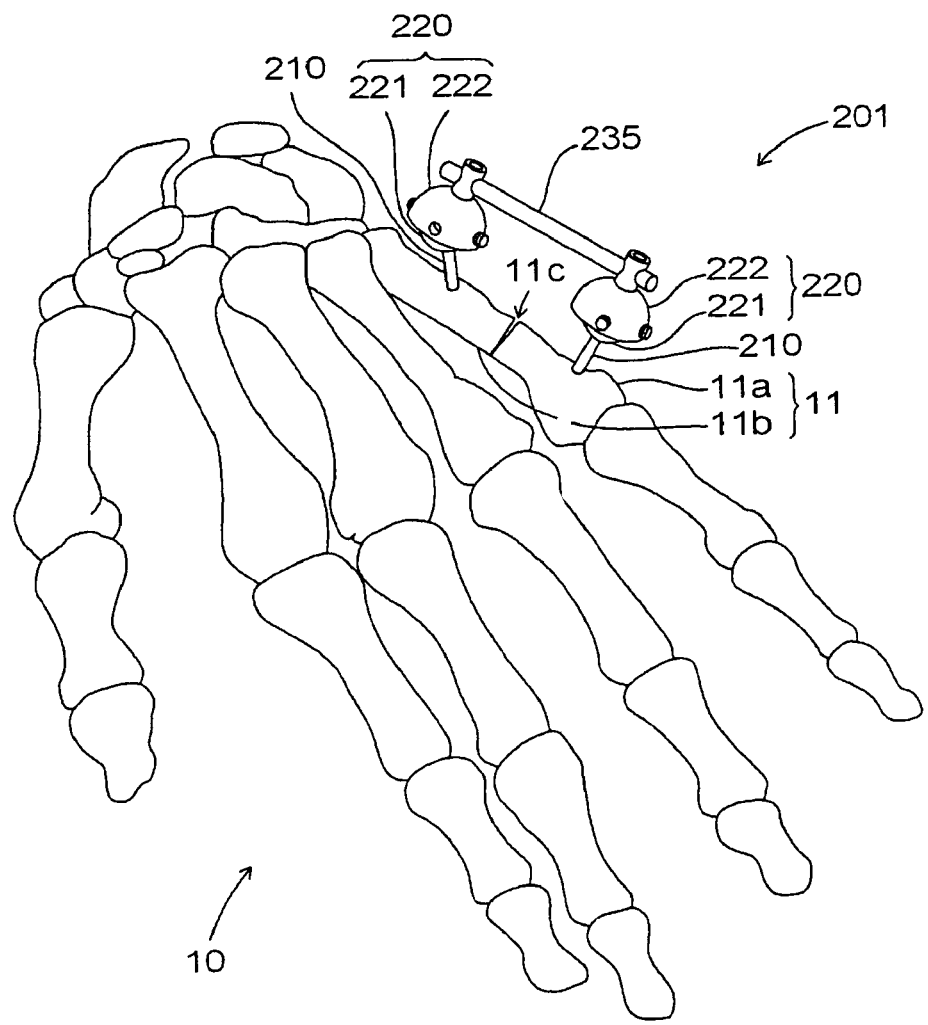
FIG. 5 is a view showing an external fixator according to an embodiment of the present invention.

FIG. 5 is a view showing an external fixator 201 according to an embodiment where a coupling member is composed of a columnar member. In FIG. 5, the same structures as those of the above-mentioned embodiment are indicated by the same reference numerals. In the embodiment shown in FIG. 5, a coupling member 235 is employed instead of the above-mentioned coupling member 230 and the coupling member 235 is a columnar member. Accordingly, it is possible to provide the external fixator 201 by using very simple structure.

It is possible to connect the sockets 222 to arbitrary positions of the coupling member 235 in this structure. Accordingly, even though the pins 210 are inserted into the bone in any direction, it is very easy to fit the sockets 222 to the balls 221 connected to the pins 210. Therefore, it is possible to very easily fix the external fixator 201 regardless of the insertion direction of the pin 210.

Meanwhile, when one coupling member 235 is composed of one member, only the connection portions of the coupling member 235 connected to the ball joints may be formed in a columnar shape. For example, a portion of the coupling member between two connection portions may be formed in the shape of a prism or the combination of several plates.

Figure 6:
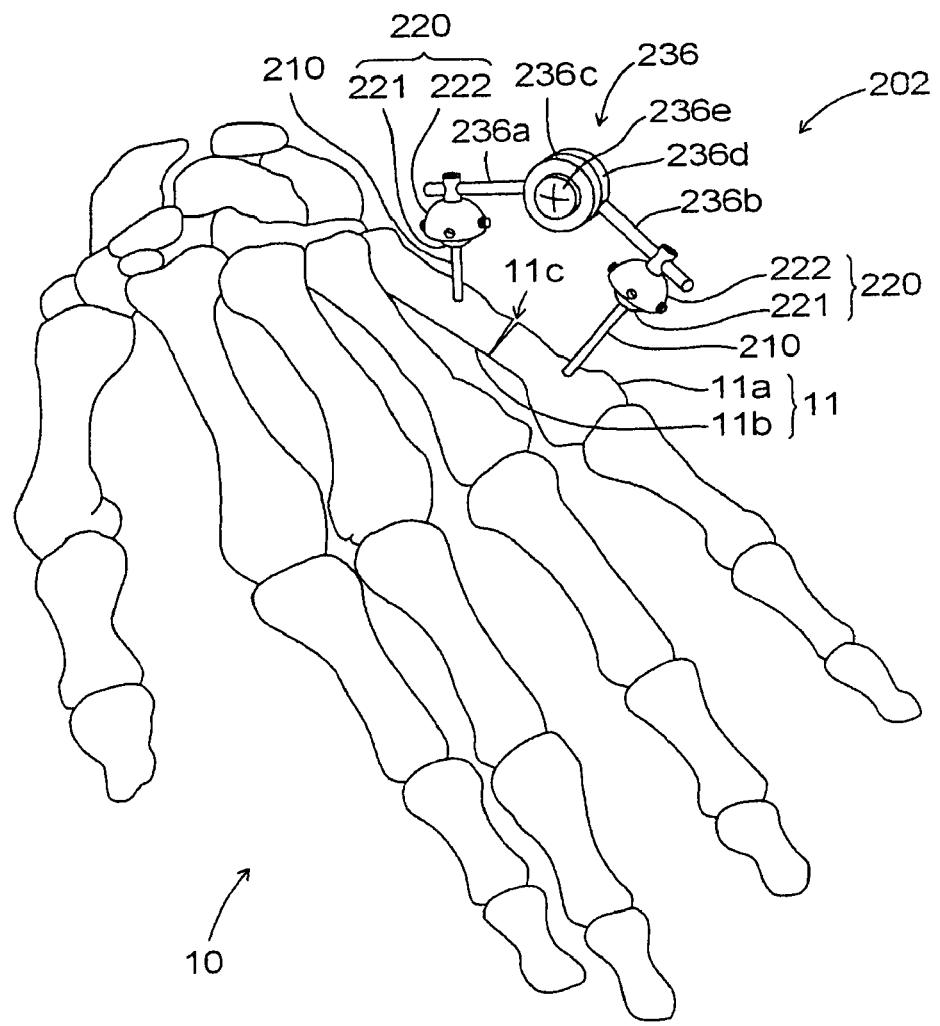
FIG. 6 is a view showing an external fixator according to an embodiment of the present invention.

In addition, there may be employed a structure where a degree of freedom is given to the direction of a coupling member. FIG. 6 is a view showing an external fixator 2020 according to an embodiment where a degree of freedom is given to the direction of a coupling member. Even in FIG. 6, the same structures as those of the above-mentioned embodiment are indicated by the same reference numerals. In this embodiment, a coupling member 236 is composed of two rod-like members 236a and 236b and rotating mechanisms 236c to 236e.

The rod-like member 236a is connected to an annular member 236c, and the rod-like member 236b is also connected to an annular member 236d. Further, a screw 236e may be inserted into holes of the annular members 236c and 236d, and the annular members 236c and 236d may be connected and fixed to each other by a nut (not shown). Accordingly, if the annular members 236c and 236d are aligned with each other and the screw 236e is inserted into the holes thereof, the rod-like members 236a and 236b can be rotated about the screw 236e on a common plane.

Furthermore, each of the rod-like members 236a and 236b has a columnar shape. Accordingly, when the rod-like members 236a and 236b are connected to the sockets 222, it is possible to arbitrarily select the positions of the connection portions therebetween. Therefore, even though the pins 210 are inserted into the bone in any direction, it is possible to very easily fit the external fixator 202 by adjusting the rotation angles of the rod-like members 236a and 236b, adjusting connection positions where the rod-like members 236a and 236b are connected to the sockets 222, and directions when the balls 221 are fitted to the sockets 222.

In this embodiment, a method of fixing the annular members 236c and 236d is not limited to a method using the combination of the screw 236e and the nut. As long as the annular members 236c and 236d can be rotated with respect to each other, various structures may be employed. Further, the rod-like members 236a and 236b are rotated on the common plane in this embodiment, but may be formed to be rotated with a higher degree of freedom by using ball joints and the like.

Figure 7:
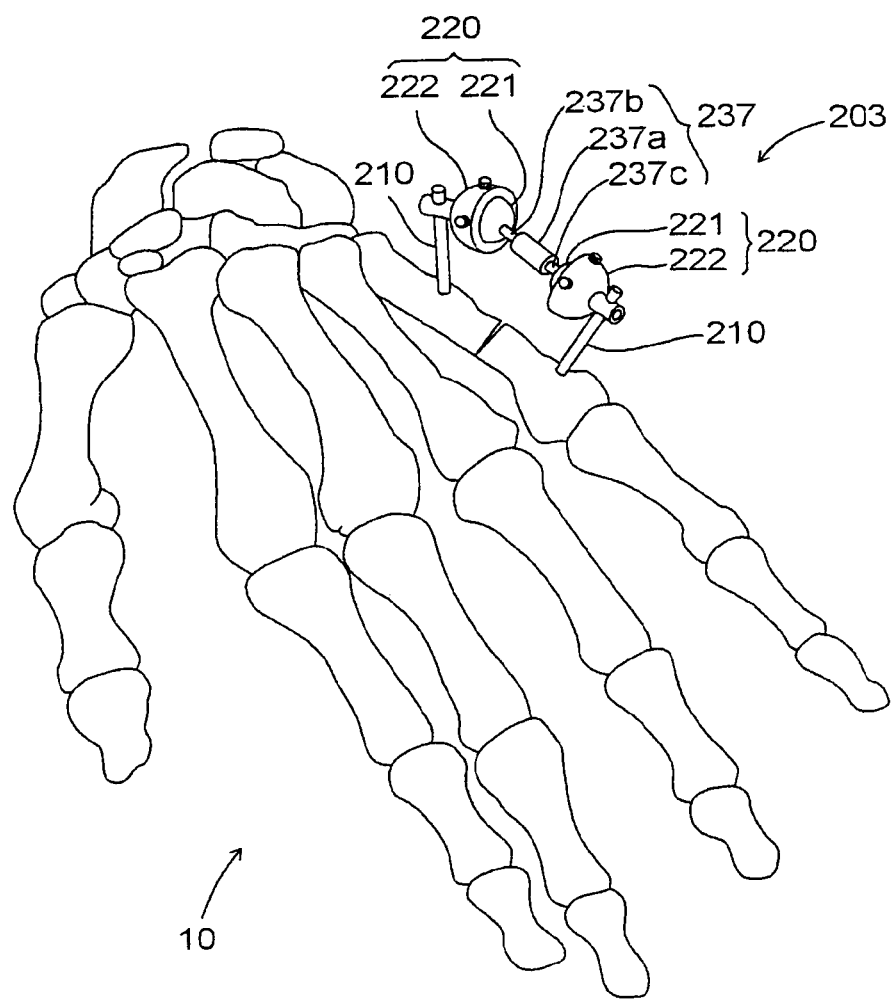
FIG. 7 is a view showing an external fixator according to an embodiment of the present invention.

In addition, the structure for connecting the socket of the ball joint may be applied to the pin. FIG. 7 is a view showing an external fixator where a socket of a ball joint is connected to a pin. In FIG. 7, the same structures as those of the above-mentioned embodiment are indicated by the same reference numerals. That is, the structure of a pin 210 and a ball joint 220 are the same as that of the pin and the ball joint of the above-mentioned embodiment, but a method of connecting the ball joint 220 to the pin 210 and the structure of a coupling member are different from those of the above-mentioned embodiment.

Specifically, the socket 222 of the ball joint 220 is connected to the pin 210. The pin 210 is inserted into an insertion portion 222f of the socket 222, and the socket 222 is fixed to the pin 210 by a hexagon socket set screw 222h. Adjustment, where the diameter of the insertion portion 222f is aligned with the diameter of the pin 210, may be appropriately performed.

A coupling member of this embodiment includes a first rod-like member 237a, a second rod-like member 237b, and a third rod-like member 237c. Like in the above-mentioned embodiment, the first rod-like member 237a is a substantially cylindrical member, and each of the second and third rod-like members 237b and 237c is a substantially columnar member. Further, thread grooves having opposite directions are formed on the inner walls of both ends of the first rod-like member 237a, and thread grooves corresponding to the thread grooves of the first rod-like member are formed on one end portion of each of the second and third rod-like members 237b and 237c.

Accordingly, if the second and third rod-like members 237b and 237c are screwed to the first rod-like member 237a, it is possible to form a coupling member 237 of which the length can be adjusted by the rotation of the first rod-like member 237a. End portions of the second and third rod-like members 237b and 237c opposite to the thread grooves can be inserted into holes of balls 211, and the second and third rod-like members 237b and 237c can be fixed to the balls 221 by hexagon socket set screws 221c.

The diameter of each of the holes 221a or the diameter of each of the second and third rod-like members 237b and 237c may be appropriately determined even in this case. Meanwhile, in this embodiment, portions where the balls 221 and the second and third rod-like members 237b and 237b are connected to each other correspond to connection portions. Since it is possible to adjust the length of the coupling member 237 by rotating the first rod-like member 237a as described above, it is possible to also change the positions of the connection portions in a longitudinal direction of the coupling member 237 in this embodiment.

When the socket 222 is connected to the pin 210 in the above-mentioned structure, the socket 222 can be freely rotated about the pin 210. Further, while the balls 221 are fixed to the second and third rod-like members 237b and 237c, it is possible to adjust the length of the coupling member 237. Accordingly, even though the pins 210 are inserted into the bone in any manner, it is possible to completely fix the external fixator 203 by adjusting the directions of the sockets 222 and the length of the coupling member 237.

In addition, one pin 210 is inserted into each of the separated bones 11a and 11b in the above-mentioned embodiment. However, a plurality of pins 210 may be inserted into a bone, and two arbitrary pairs thereof may be connected by ball joints or coupling members. In addition, one pin 210 may be inserted into a plurality of bones. For example, in FIG. 1, the pin 210 may pass through the bone 11a, and the pin 210 passing through the bone 11a may be further inserted into the bone 11b in order to reset the bones. That is, a method of inserting the pins 210 may be appropriately changed according to the state of the broken bone, the size of the bone, the strength required to reset bones, etc.

Further, each of the members has been fixed using hexagon socket set screws in the above-mentioned embodiment. However, each of the members may be fixed using slotted set screws and may be fixed using various means other than screws. For example, the connection between the ball 221 and the pin 210 or the connection between the ball 221 and the socket 222 may be performed by fitting. In addition, the substantially semi-spherical body 222a having the substantially semi-spherical recess 222c has been exemplified in the above-mentioned embodiment. However, as long as the ball can be freely rotated while being disposed in the recess, the recess may have any shape without being limited to the semi-spherical shape. Further, the shape of the body 222a is not limited to the semi-spherical shape, and the body may employ various structures such as a rectangular shape.

Figure 8:
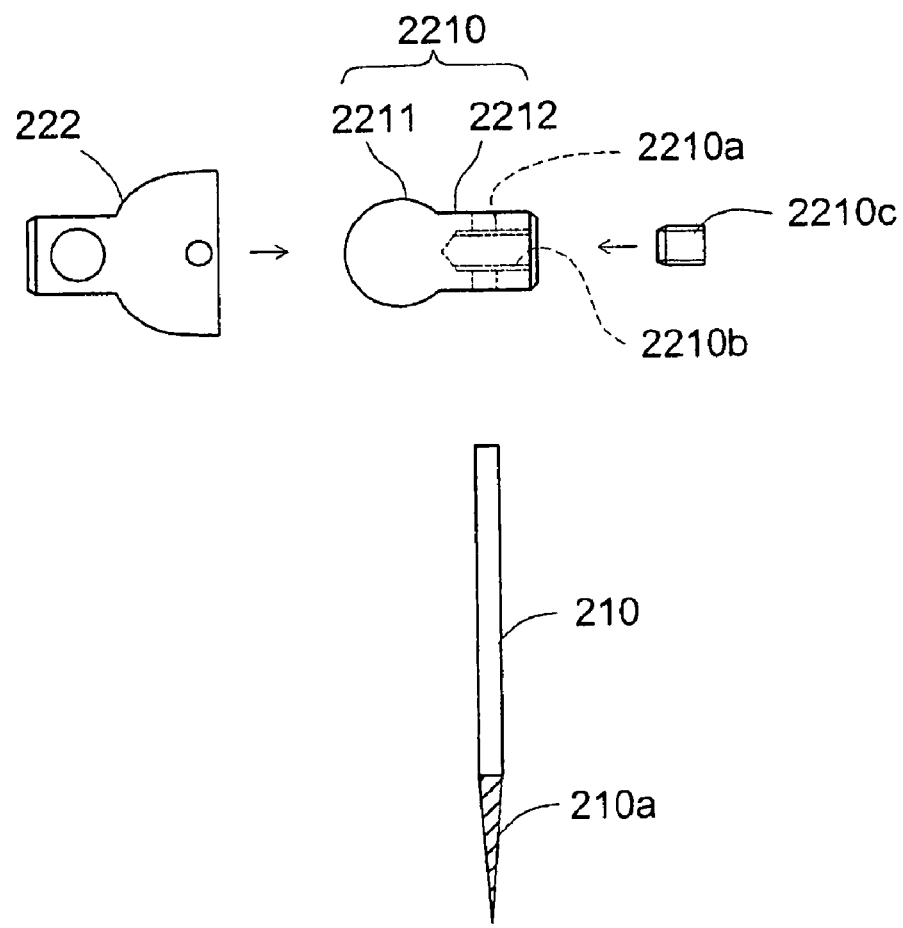
FIG. 8 is a view illustrating the structure of a pin and a ball according to an embodiment of the present invention.

Next, an embodiment where a plurality of ball joints are connected to each pin will be described. In this embodiment, the above-mentioned ball joint 220 (hereinafter, referred to as an end joint), which includes the ball 221 and the socket 222, is connected to the end of a pin 210. Another ball joint (hereinafter, referred to as an intermediate joint) is provided between the end joint and a thread groove 210a of the pin 210. FIG. 8 is a view showing a rotary member 2210 that connects the intermediate joint to the pin 210.

The rotary member 2210 has the structure where a ball 2211 and a cylindrical insertion portion 2212 are connected to each other as shown in FIG. 8. Since the ball 2211 can be fitted to the above-mentioned socket 222, it is possible to rotate the socket 222 around the outer periphery of the ball 2211 while the socket 222 and the ball 2211 are in contact with each other, and to fix the socket to the ball by screws.

Meanwhile, the insertion portion 2212 includes a hole 2210a that extends in a direction orthogonal to an axis of the insertion portion and passes through the insertion portion 2212, and a screw hole 2210b that is formed parallel to the axis of the insertion portion. The hole 2210a is a hole into which the pin 210 is inserted, and the screw hole 2210b is a screw hole to which the pin 210 inserted into the hole 2210a is fixed by screws.

That is, the inner diameter of the hole 2210a is substantially equal to the outer diameter of the pin 210. Accordingly, it is possible to fit the pin 210 into the hole 2210a. Further, while being fitted into the hole 2210a, the pin 210 is fixed by a hexagon socket set screw 2210c inserted into the screw hole 2210b.

Figure 9:
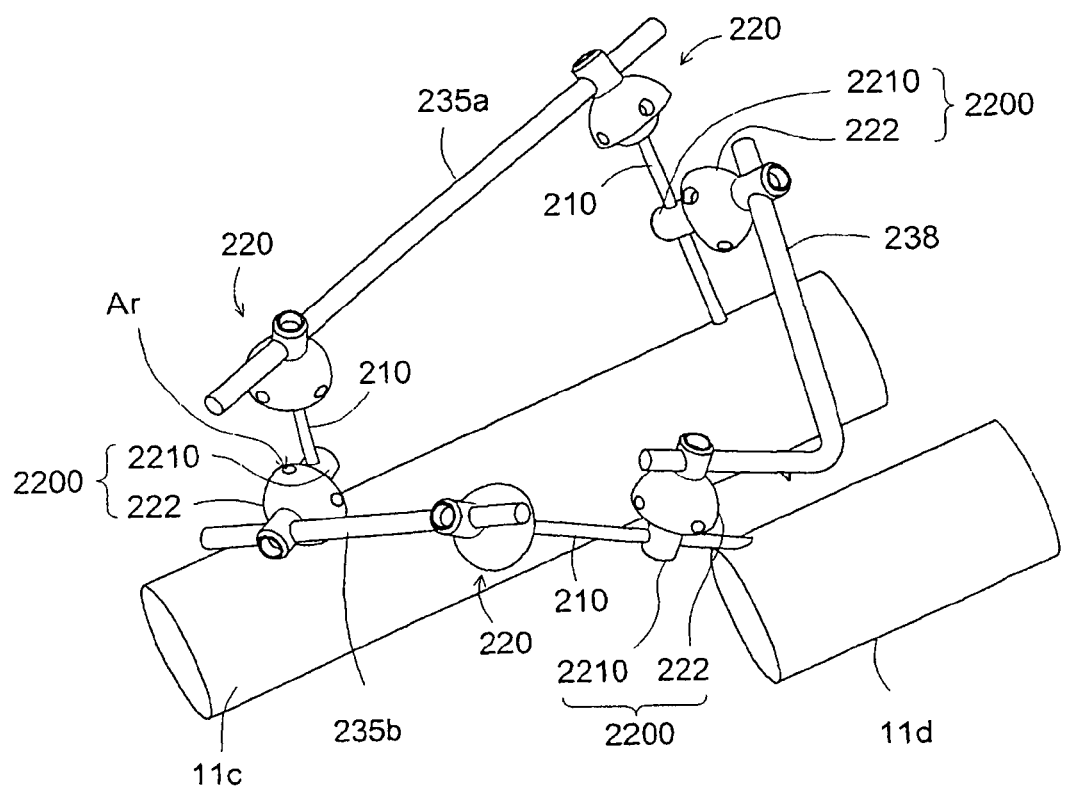
FIG. 9 is a view showing an external fixator according to an embodiment of the present invention.

FIG. 9 is a schematic view showing a usage example of the external fixator according to this embodiment. FIG. 9 shows that three pins 210 are inserted into bones 11c and 11d. In this case, two pins 210 are inserted into the bone 11c, one pin 210 is inserted into the bone 11d, and an end joint (ball joint 220) and an intermediate joint (ball joint 2200) are connected to each of the pins.

That is, the end joint includes a ball 221 and a socket 222 like the ball joint shown in FIG. 1, and is connected to the end of each of the pins. In this embodiment, before the end joint is connected to the pin 210, the intermediate joint including a rotary member 2210 and a socket 222 is connected to the pin 210.

More specifically, for example, it is possible to try using the external fixator according to the following procedure. After the pins 210 are inserted into the bones 11c and 11d, the rotary member 2210 is connected to each of the pins 210 and the rotary members 2210 are temporarily fixed between the ends of the pins 210 and the bones 11c and 11d by the hexagon socket set screws 2210c. Further, while the rotary members 2210 are fitted to the sockets 222, respectively, the rotary members 2210 and the sockets 222 are temporarily fixed to each other.

After that, like in FIG. 1, the ball 221 is connected to the end of each of the pins 210 and fitted to each of the sockets 222. Then, coupling members 235a, 235b, and 238 are inserted into the sockets 222, respectively, and temporarily fixed to the sockets. When the coupling members are temporarily fixed to the sockets, it is possible to adjust the directions of the rotary members 2210 and the sockets 222. Meanwhile, each of the coupling members 235a and 235b is the same as the coupling member 235 shown in FIG. 5, and the coupling member 238 is a member that is formed by bending the coupling member 235.

After the ball joints 220 and 2200 and the coupling members 235a, 235b, and 238 are temporarily fixed to each other while being connected to each other in this way, the sockets 222 and the coupling members 235a, 235b, and 238 are fixed to each other by screws. In the process for fixing the sockets to the coupling members as described above, it is possible to completely fix the external fixator after adjusting the directions of the sockets 222 or the directions of the rotary members 2210. Accordingly, when the external fixator is fixed, a very high degree of freedom is given to the insertion direction of each of the pins 210. As a result, it is possible to easily and appropriately reset bones.

Further, the directions of the coupling members of the ball joints connected to the pins 210 are not limited to one direction, and the coupling members may be connected to the pins while the directions of the coupling members are set to several directions. Accordingly, it is possible to fix the pins 210 by the coupling members that extend in several directions, to freely set the directions of the coupling members, and to maintain the external fixator while the external fixator is firmly fixed.

For example, even though a force is applied to the two pins 210 inserted into the bone 11c in an axial direction of the bone 11c (a direction where the bone 11c extends), the external fixator can remain firmly fixed due to the presence of the coupling member 235a. In addition, even though a force is applied to the two pins 210 in a radial direction of the bone 11c, the external fixator can remain firmly fixed due to the presence of the coupling members 235b and 238.

Meanwhile, the structure shown in FIG. 9 is merely illustrative. For example, the structure of the coupling member is not limited to the structure that includes the coupling members 235a, 235b, and 238, and may employ the above-mentioned various coupling members. Further, the size of each of the ball joints 220 and 2200 may be appropriately determined according to the size of a bone to be reset, and may vary by the position of the pin 210.

In addition, in FIG. 9, screws have been omitted for simple drawing. However, each of the screws is not limited to a hexagon socket set screw, and various screws may be employed as the screws. Meanwhile, the structure of the socket 222 of this embodiment is the same as the structure shown in FIG. 3, screw holes are formed on the periphery of the socket 222 at regular intervals (at four positions in this embodiment), and axes of the screw holes intersect at the center of the recess 222c. Accordingly, hexagon socket set screws 222e can be screwed to the socket 222 in several directions. As a result, it is very easy to fix the external fixator.

For example, since the coupling member 235a is formed near a screw hole 222d indicated by an arrow Ar in the embodiment shown FIG. 9, it is difficult to screw the hexagon socket set screw 222e to the screw hole 222d. However, it is very easy to select a screw hole 222d where the screw 222e is easily screwed to another screw hole 222d. Accordingly, according to this embodiment, it is possible to easily fix the external fixator regardless of the state where the external fixator is fixed.

In addition, two linear coupling members 235a and 235b and one bent coupling member 238 are used in the embodiment shown in FIG. 9. However, the shapes of the coupling members are not limited thereto. For example, a coupling member of which a portion except for both ends is curved may be employed. If this coupling member is employed, pins can be inserted into a substantially columnar bone, such as a finger or an arm, in substantially opposite directions, and ball joints connected to the pins can be connected to each other by the coupling member. In addition, the structure where a plurality of ball joints are connected to one pin as described above may be achieved by structure other than the structure shown in FIGS. 8 and 9. For example, a member, which is connected to the pin of the above-mentioned intermediate joint, may be formed of the socket 222 as shown in FIG. 7.

Next, a ball joint 320 shown in FIGS. 10 and 11 will be described. The ball joint 320 fixes a pin 210 with a coupling member 235 and is connected to another ball joint 320 (not shown) by the coupling member 235. The ball joint 320 is substituted with the above-mentioned ball joint, so that various external fixators may be formed. That is, as for the structure of the external fixator except for the ball joint, the structure of the above-mentioned embodiment may be applied to the ball joint 320.

A rotary member 321 is a ball having a hole 321a into which the pin 210 is inserted, and a screw hole 321b to which the pin 210 is fixed by a screw. While being inserted into the hole 321a, the pin 210 is fixed by the set screw 321c screwed to the screw hole 321b.

A first screw 322b, which forms a male thread, is formed at a supporting member 322. A first supporting portion 322a, by which the rotary member 321 is rotatably supported, is formed at the end portion of the first screw 322b. The first supporting portion 322a is a recessed surface that has a curvature radius substantially equal to the radius of the rotary member 321. It is preferable that the first supporting portion 322a has a shape to be supported at three points together with the rotary member 321. Further, it is preferable that the centroid of the three points pass through an axis of rotation of the first screw 322b and a plane including the three points be perpendicular to the axis of rotation of the first screw 322b. It is more preferable that the centroid of four or more contact points correspond to the center of the rotary member 321. If the supporting portion 322a is a recessed surface that has a curvature radius substantially equal to the radius of the rotary member 321, a centroid of contact points corresponds to the center of the rotary member 321.

A through hole 322c and a screw hole 322d, which are used to fix the coupling member 235, are formed at the supporting member 322. The coupling member 235 is inserted into the through hole 322c, and is fixed to the supporting member 322 by a screw (not shown) that is screwed to the screw hole 322d.

A fastening member 323 has a tubular shape, has openings at both end portions thereof, and receives the rotary member 321. That is, the fastening member 323 has a tubular shape where the diameter R1 (see FIG. 12A) of one opening is larger than the diameter of the rotary member 321. Further, the fastening member 323 is a specific nut, and the outer surface of the fastening member has the shape of side surfaces of a substantially hexagonal column that can be held by a spanner.

A second screw 323a, which forms a female thread corresponding to the first screw 322b, is formed at one end portion of the fastening member 323. The miner diameter of the second screw 323a is designed to be larger than that the diameter of the rotary member 321. Accordingly, the fastening member 323 can receive the rotary member 321. Meanwhile, the relationship between the female and male threads of the fastening member 323 and the supporting member 322 may be reversed. That is, a male thread is formed on the outer surface of the fastening member 323, and a female thread may be formed on the inner surface of the supporting member 322.

Figure 12A:
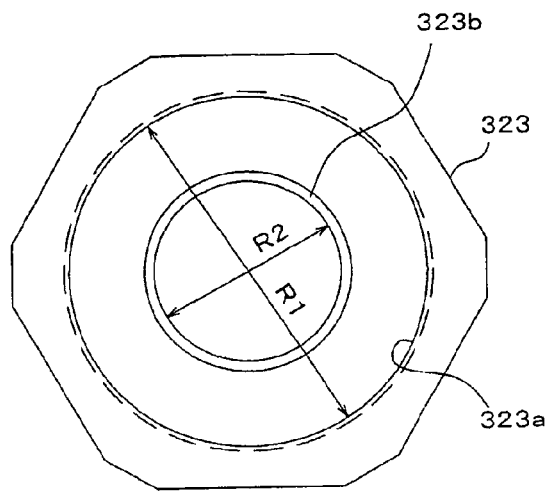
FIG. 12A is a plan view of a fastening member according to an embodiment of the present invention.

A second supporting portion 323b, which can support the rotary member 321 at least three points, is formed at the other end portion of the fastening member 323. The second supporting portion 323b is a portion that protrudes toward a central axis of the fastening member 323. The inner end of the second supporting portion 323b has a circular shape as shown in FIG. 12A. Since an inner diameter R2 of the second supporting portion 323b is designed to be smaller than the diameter of the rotary member 321, the second supporting member 323b can support the rotary member 321 at least three points. An end face of the second supporting portion 323b close to the second screw 323a (upper side of a plane of FIG. 10) has a tapered shape and the diameter of the end face is increased toward the open end of the fastening member 323 close to the second screw 323a.

Figure 12B:
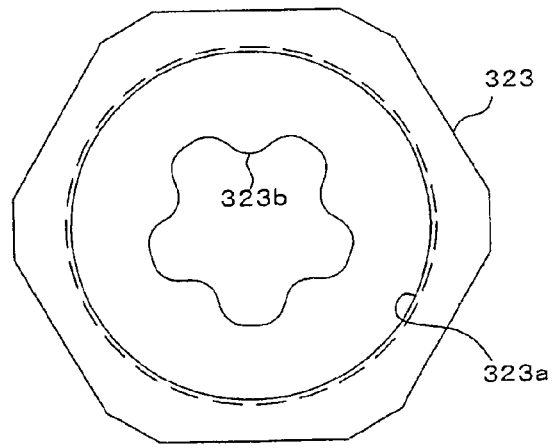
FIG. 12B is a plan view of a fastening member according to an embodiment of the present invention.

As long as the second supporting portion 323b can press the rotary member 321 against the first supporting portion 322a, the second supporting portion may have any shape. For example, the second supporting portion may have a shape that has a plurality of convex portions as shown in FIG. 12B. It is preferable that a centroid of contact points between the rotary member 321 and the first and second supporting portions 322a and 323b always correspond to the center of the rotary member 321 when the second screw 323a is screwed to the first screw 322b while the rotary member 321 is in contact with the first and second supporting portions 322a and 323b. Accordingly, it is preferable that the second supporting portion 323b have a shape to support the rotary member 321 at least three points of which a centroid is positioned on the central axis of the second screw 323a on a plane perpendicular to the central axis of the second screw 323a. In this case, if only one member (fastening member) is rotated, forces required for adjusting an attitude of the coupling member 235 with respect to the pin 210 can be fixed while being simultaneously adjusted for the attitude change in all directions. Further, in this case, if only one member (fastening member) is rotated, forces for fixing the attitude of the coupling member 235 with respect to the pin 210 can be simultaneously increased for the attitude change in all directions. As a result, it is easier to fix bones by the external fixator.

However, for example, if the first supporting portion 322a and the rotary member 321 are in contact with each other at three or more points and these contact points are positioned on a plane perpendicular to the axis of rotation of the first screw 322b, the rotary member 321 can be pressed against the first supporting portion 322a at one point of the second supporting portion 323b. The sufficient condition in this case is that a straight line, which passes through the contact point between the second supporting portion 323b and the rotary member 321 and is parallel to the central axis of the second screw 323a, may pass through the inside of a polygon whose apexes are the contact points between the first supporting portion 322a and the rotary member 321 and the central axis of the second screw 323a may pass through the inside of the polygon. In this case, when the second screw 323a is screwed to the first screw 322b while the rotary member 321 is in contact with the first and second supporting portion 322a and 323b, the centroid of the contact points between the rotary member 321 and the first and second supporting portions 322a and 323b always corresponds to the center of the rotary member 321.

An end face of the second supporting portion 323b distant from the second screw 323a (lower side of a plane of FIG. 10) has a tapered shape and the diameter of the end face is increased toward the open end of the fastening member 323 where the second supporting portion 323b is formed. If the end face of the second supporting portion 323b is designed to have such a tapered shape, the operation range of the pin 210 broadens.

Next, the usage of the external fixator, which includes the ball joint 320 having the above-mentioned structure, will be described with reference to FIGS. 13A to 13H.

Figure 13A:
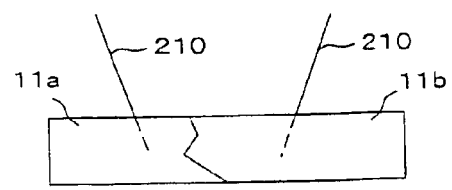
FIG. 13A is a schematic view illustrating the usage of an external fixator according to an embodiment of the present invention.

First, the ends of the pins 210 are inserted into broken bones 11a and 11b by using a drill and then fixed to the bones, respectively (FIG. 13A).

Figure 13B:
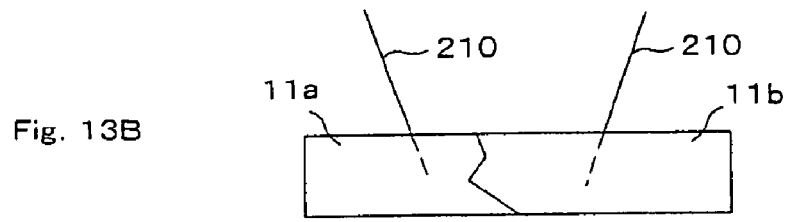
FIG. 13B is a schematic view illustrating the usage of an external fixator according to an embodiment of the present invention.

After that, each of the pins 210 is cut to a desired length (FIG. 13B).

Figure 13C:
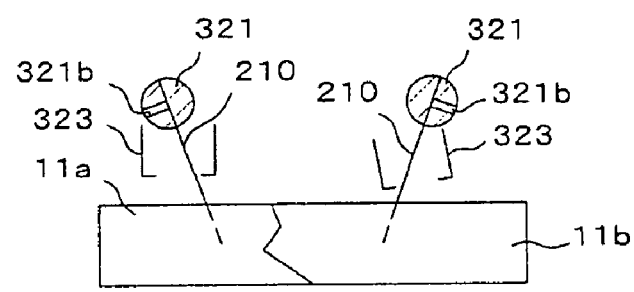
FIG. 13C is a schematic view illustrating the usage of an external fixator according to an embodiment of the present invention.

Subsequently, the fastening member 323 is fitted to each of the pins 210 in an appropriate direction, and the rotary member 321 is fixed to the end of each of the pins 210 by using the set screw 321b (FIG. 13C).

Figure 13D:
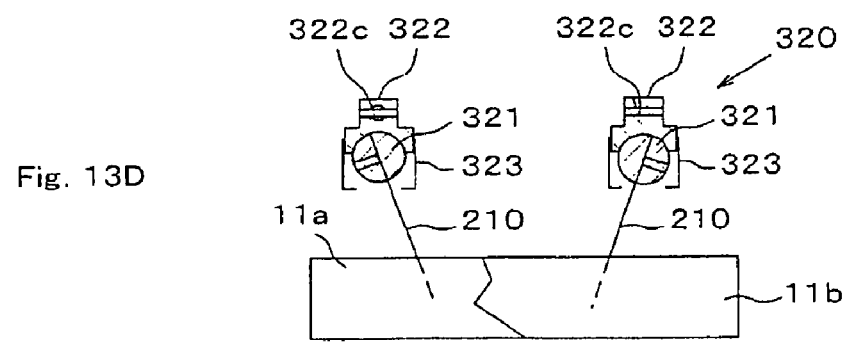
FIG. 13D is a schematic view illustrating the usage of an external fixator according to an embodiment of the present invention.

Next, the supporting member 322 and the fastening member 323 are loosely fastened to each other with the rotary member 321 interposed therebetween (FIG. 13D). In this state, the ball joint 320 is allowed to freely move.

Figure 13E:
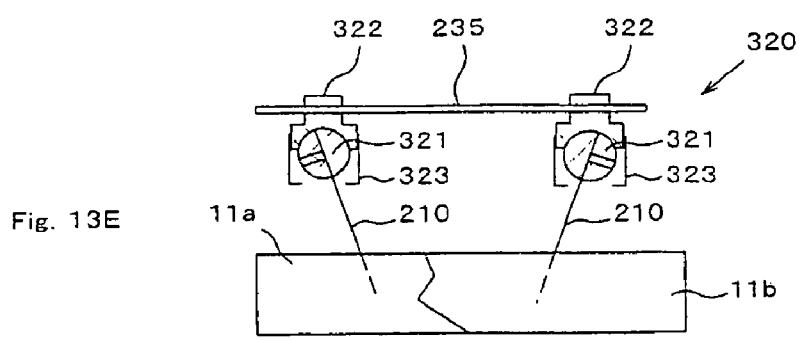
FIG. 13E is a schematic view illustrating the usage of an external fixator according to an embodiment of the present invention.

Then, the coupling member 235 is inserted into the through hole 322c of each of the supporting members 322 (FIG. 13E). Since the ball joint 320 can freely move and the position of the connection portion between the coupling member 235 and the ball joint 320 can be freely adjusted at this time, it is easy to insert the coupling member 235 into the through hole 322c of the supporting member 322. When the ball joint 320 is allowed to freely move and the coupling member 235 is only inserted into the through hole 322c without being fixed, it is possible to freely adjust the bonding state of the broken bones 11a and 11b.

Figure 13F:
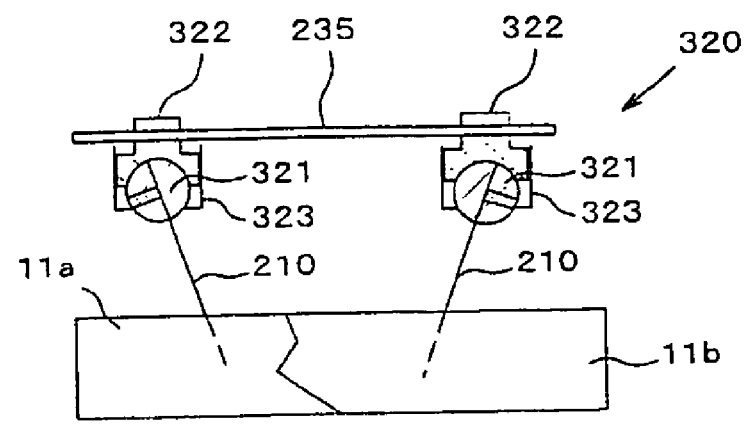
FIG. 13F is a schematic view illustrating the usage of an external fixator according to an embodiment of the present invention.

After that, while the coupling member 235 is held, the fastening member 323 is fastened to the supporting member 322 by using a wrench or the like (FIG. 13F). That is, the second screw of the fastening member 323 is fastened to the first screw of the supporting member 322. In this case, since the fastening member 323 is much larger than, for example, the set screw 222e shown in FIG. 3, it is easy to rotate the fastening member 323 by the wrench. Further, while each of the rotary members 321 is in contact with the fastening member 323 and the supporting member 322, it is possible to uniformly adjust forces, which are required for adjusting an attitude of the coupling member 235 with respect to the pin 210, in all directions by adjusting the amount of fastening of the fastening member 323. In this state, if the clearance between the coupling member 323 and the through hole 322c is negligibly small, it is possible to uniformly adjust forces, which are required for adjusting the bonding state of the broken bones 11a and 11b, in all directions.

Further, while the fastening member 323 of one ball joint of two ball joints 320, which are connected to each other by the coupling member 235, is excessively fastened to the supporting member 322, the coupling member 235 cannot be rotated. Accordingly, it is possible to adjust the amount of fastening of the fastening member 323 of the other ball joint 320 with one hand. That is, the coupling member 235 does not need to be held in this state. Therefore, while adjusting the amount of fastening of the fastening member 323 with one hand, it is possible to handle an affected part. In addition, if the clearance between the coupling member 323 and the through hole 322c is negligibly small, the attitude and position of one bone of the broken bones 11a and 11b is not substantially changed with respect to those of the other bone while the fastening members 323 of the two ball joints 320, which are connected to each other by the coupling member 235, are excessively fastened. Accordingly, while confirming the bonding state of the broken bones 11a and 11b by using an X-ray image, a person in charge can fix the broken bones 11a and 11b in an appropriate bonding state all by himself.

Figure 13G:
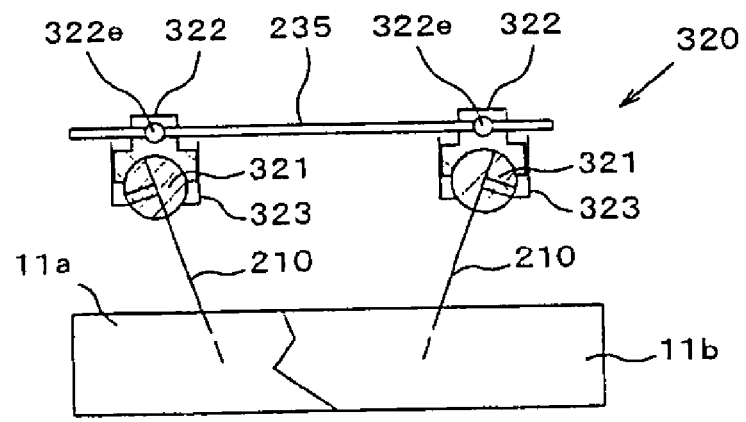
FIG. 13G is a schematic view illustrating the usage of an external fixator according to an embodiment of the present invention.

After that, when the broken bones 11a and 11b are appropriately bonded, the coupling member 235 is fixed to each of the supporting members 322 by using a set screw 322e (FIG. 13G). Therefore, it is possible to completely fix the reset state of the broken bones 11a and 11b.

Figure 13H:
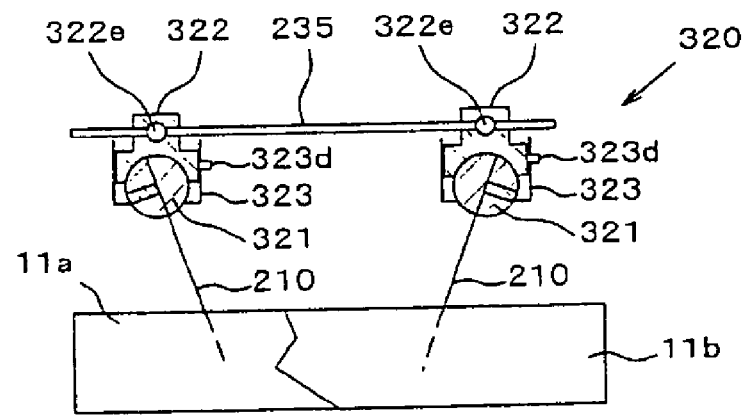
FIG. 13H is a schematic view illustrating the usage of an external fixator according to an embodiment of the present invention.

After that, as shown in FIG. 13H, it is preferable that a third screw 323d be screwed to a screw hole formed at the fastening member 323 so that the end of the third screw 323d presses the supporting member 322. In this case, it is more preferable that the thread of the first screw 322b of the supporting member 322 be pressed and stripped. Therefore, it is possible to reliably prevent the fastening member 323 from being loosen.

Meanwhile, in the above-mentioned various embodiments, as long as a person in charge of the treatment does not handle an affected part, the ball joint does not move. If a person in charge of the treatment handles an affected part and the ball joint can be fixed while being allowed to move, it is easier to handle the external fixator. However, it is not easy to achieve this state by adjusting the amount of fastening of the screw. Accordingly, it is preferable that the member (socket and supporting member) to which the coupling member is fixed and the member (rotary member) to which the pin is fixed attract each other by a magnetic force while being rotatable with respect to each other. In this structure, for example, the socket 222 and the ball 211 shown in FIG. 2 may be formed of ferromagnetic bodies that are magnetized so as to attract each other. Further, for example, the supporting member 322 and the rotary member 321 shown in FIG. 10 may be formed of ferromagnetic bodies that are magnetized so as to attract each other. Materials, such as ferrite, neodymium, an iron oxide, a chrome oxide, and cobalt, which are used to obtain a magnetic force required on a basis of size and mass of the external fixator, may be employed as the ferromagnetic body. Furthermore, it is preferable that an alloy be employed as the ferromagnetic body in order to obtain both strength and a magnetic force.

Further, in the above-mentioned various embodiments, if the color of the external fixator in an X-ray photograph is not so dark, it is possible to easily confirm the bonding state of the broken bones by the X-ray photograph. Accordingly, it is preferable that components of the external fixator be made of, for example, a material having X-ray transmittance higher than that of a bone. In this structure, for example, the coupling member is made of composite plastics that may be reinforced with carbon fiber, glass fiber, or the like or the ball joint may be composed of a plastic magnet. If the above-mentioned various plastics are used, it is possible to reduce the weight of the external fixator and to reduce manufacturing costs of components because injection molding can be applied. It is also possible to prevent rust. Base materials of composite plastics may be thermoplastic resins or thermosetting resins. Specifically, engineering plastics such as polycarbonate, and super engineering plastics such as polyphenylene sulfide, amorphous polyamate, an aromatic polyetherketone resin, and thermoplastic polyimide may be used. If a plastic magnet is used for the ball joint, it is possible to obtain an external fixator that allows the pin and the coupling member to be temporarily fixed by a magnetic force and allows the broken bones to be easily confirmed.

Figure 10:
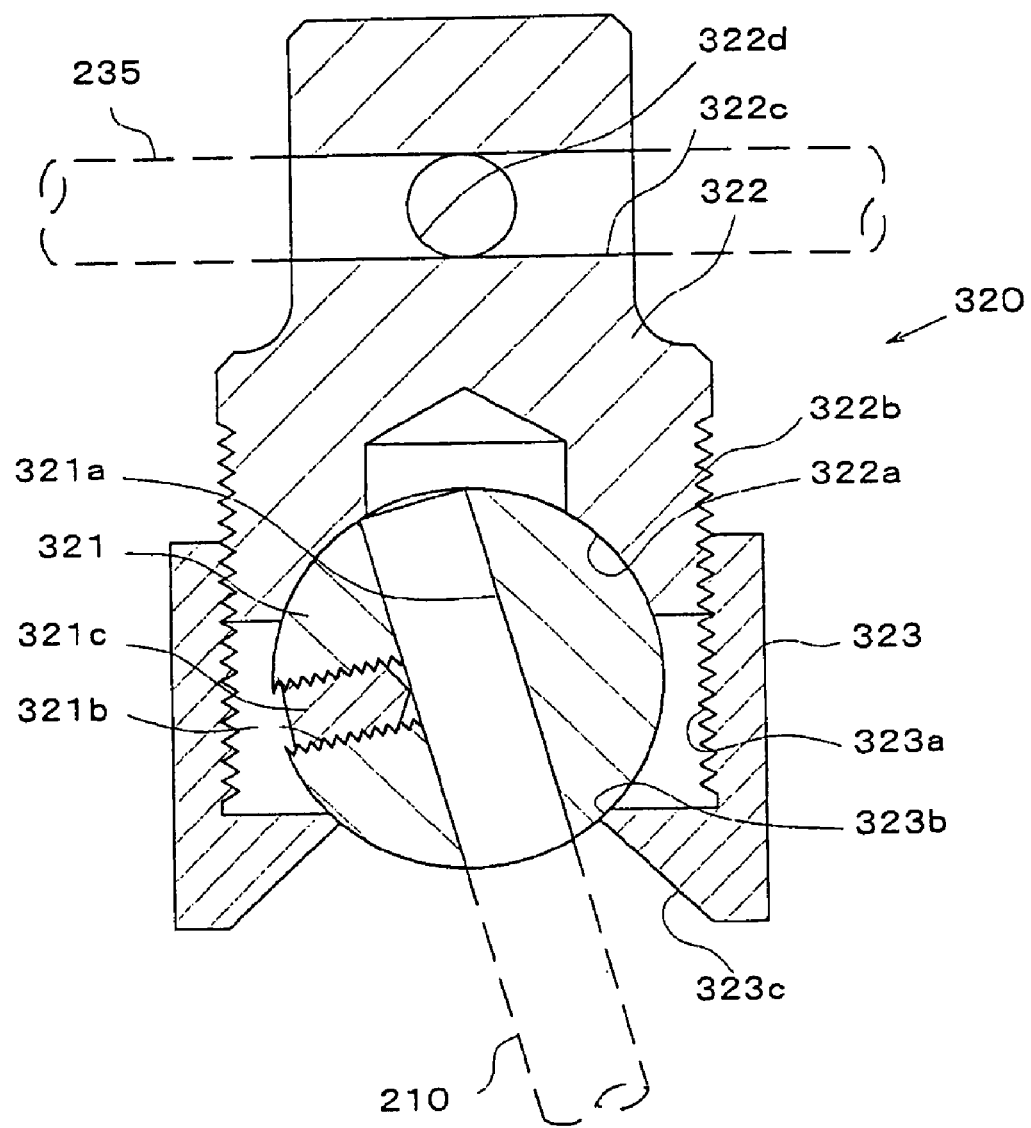
FIG. 10 is a cross-sectional view showing an external fixator according to an embodiment of the present invention.
Figure 11:
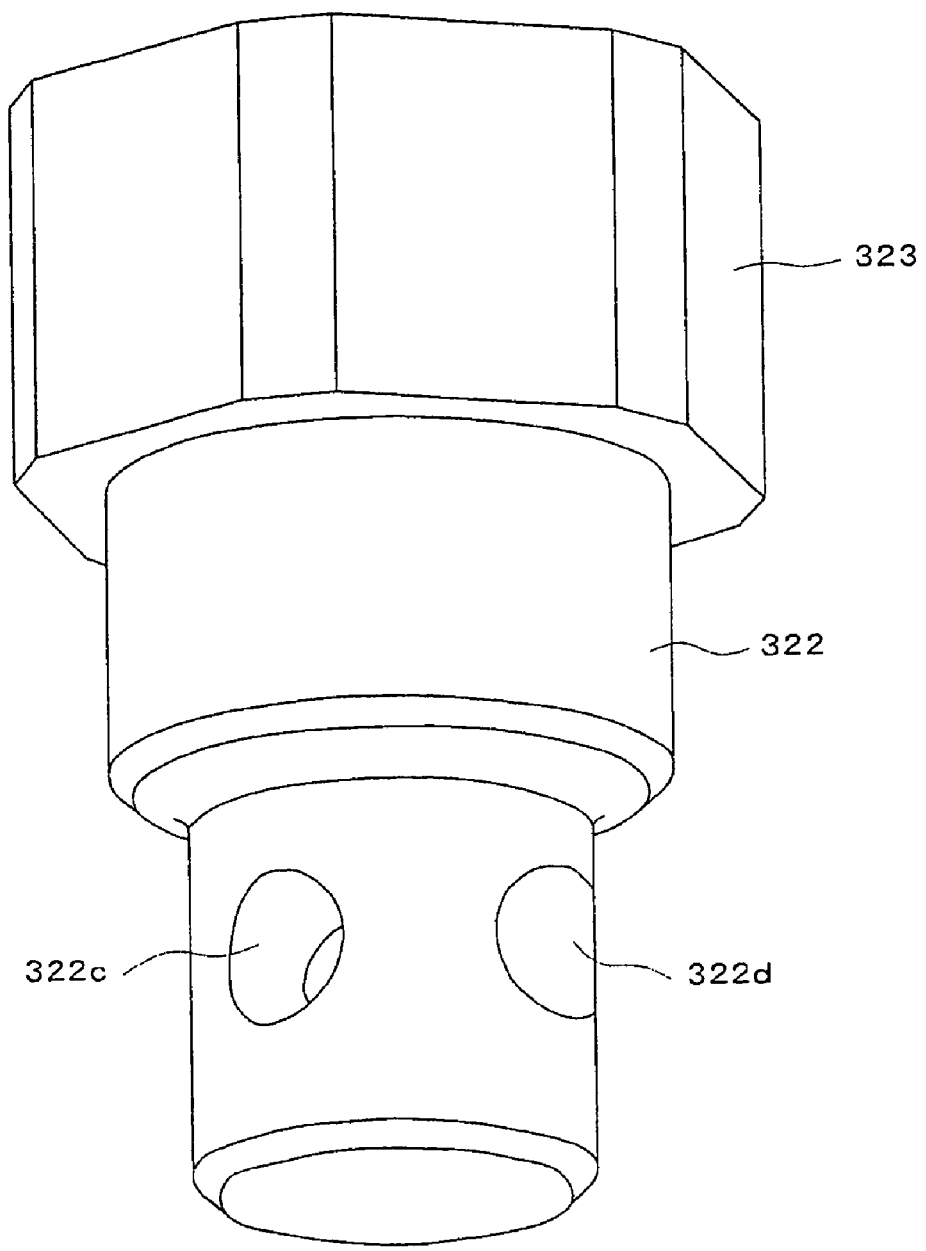
FIG. 11 is a perspective view showing an external fixator according to an embodiment of the present invention.

For example, the socket 222 and the ball 211 shown in FIG. 2 are formed of plastic magnets that are magnetized so as to attract each other or the supporting member 322 and the rotary member 321 shown in FIG. 10 are formed of plastic magnets that are magnetized so as to attract each other, so that it is possible to obtain an external fixator that allows a ball joint to be temporarily fixed by a magnetic force and allows the broken bones to be easily confirmed.

INDUSTRIAL APPLICABILITY

The present invention may be used for a treatment of broken bones. Further, the present invention may be provided as a product by a manufacturer of therapeutic devices for broken bones.

The invention claimed is:
1. An external fixator comprising:
a plurality of pins to be inserted into bones;
a coupling member, at least of a portion of which is configured as a cylindrical coupling part; and
a plurality of ball joints that fix the coupling member to the pins and are connected to each other by the coupling member, the plurality of ball joints each including:
a rotary member that is a ball;
a supporting member where a first thread and a first supporting portion that rotatably supports the ball are formed; and
a fastening member which has a tubular shape, has openings at both end portions thereof, and receives the ball, the fastening member at one end portion of which is formed a second thread corresponding to the first thread and at the other end portion of which is formed a second supporting portion that presses the ball against the first supporting portion by screwing the second thread to the first thread,
wherein the pin is fixed to the rotary member while being inserted into a hole formed at the rotary member, and
the coupling member is fixed to the supporting member with the coupling part being inserted into the supporting member, and
the rotary member and/or the supporting member is formed of a plastic magnet.

2. The external fixator according to claim 1,
wherein the hole is formed at a single member forming the entire rotary member.

3. The external fixator according to claim 1
wherein the rotary member is small enough to go through one of the openings of the fastening member until being in contact with the second supporting portion.

4. The external fixator according to claim 1,
wherein the hole formed at the rotary member passes through the rotary member.

5. The external fixator according to claim 1,
wherein the pin inserted into the hole is fixed to the rotary member by a screw screwed to a screw hole that leads to the hole formed at the rotary member.

6. The external fixator according to claim 1,
wherein, when the second thread is screwed to the first thread, the second supporting portion presses the ball against the first supporting portion while supporting the ball at three points, and
when the ball is in contact with the first and second supporting portions, a centroid of contact points between the ball and the first and second supporting portions always corresponds to the center of the ball.

7. The external fixator according to claim 1, further comprising:
a third screw which is screwed to one, which is provided outside, of the fastening member and the supporting member to thereby press the other provided inside, and fixes the fastening member to the supporting member so that the fastening member and the supporting member are not rotated.

8. The external fixator according to claim 1,
wherein the plurality of ball joints are fixed to each of the pins.

9. The external fixator according to claim 1,
wherein the coupling member includes a plurality of connection portions that connect the ball joints, and
the positions of the plurality of connection portions are adjusted at least in a longitudinal direction of the coupling member.

10. The external fixator according to claim 1,
wherein the coupling member includes a first rod-like member and second and third rod-like members that are connected to both ends of the first rod-like member by screw mechanisms, and
one of the screw mechanisms provided at the both ends is a right-hand thread and the other thereof is a left-hand thread.

11. The external fixator according to claim 1,
wherein the coupling member includes two rod-like members and the two rod-like members are connected so as to be rotated on at least a plane between two of the ball joints that are connected to each other by the coupling member.

12. An external fixator comprising:
a plurality of pins that are inserted into bones;
a coupling member, at least a portion of which is configured as a cylindrical coupling part; and
a plurality of ball joints that fix the coupling member to the pins and are connected to each other by the coupling member, the plurality of ball joints each including:
a rotary member, at least a part of the rotary member being a ball;
a socket having a recess in which a centroid of the ball is disposed and a screw hole that reaches the recess from an outer surface; and
a screw that is screwed to the screw hole to thereby press the ball against the recess,
wherein the pin is fixed to the rotary member while being inserted into a hole formed at the rotary member,
the coupling member is fixed to the supporting member with the coupling part being inserted into the supporting member, and
the rotary member and/or the socket is formed of a plastic magnet.

13. The external fixator according to claim 12,
wherein any one of the rotary member and the socket of at least one of the ball joints is fixed to the end of the pin, and the other of the rotary member and the socket is fixed to the fixed rotary member or socket.

14. The external fixator according to claim 12,
wherein the ball joint includes an insertion portion, where a through hole is formed, at any one of the rotary member and the socket, and
the pin is inserted into and fixed to the through hole of the insertion portion.

15. The external fixator according to claim 12,
wherein the plurality of ball joints are fixed to each of the pins.

16. The external fixator according to claim 12,
wherein the coupling member includes a plurality of connection portions that connect the ball joints, and
the positions of the plurality of connection portions are adjusted at least in a longitudinal direction of the coupling member.

17. The external fixator according to claim 12,
wherein the coupling member includes a first rod-like member and second and third rod-like members that are connected to both ends of the first rod-like member by screw mechanisms, and
one of the screw mechanisms provided at the both ends is a right-hand thread and the other thereof is a left-hand thread.

18. The external fixator according to any one of claim 12,
wherein the coupling member includes two rod-like members and the two rod-like members are connected so as to be rotated on at least a plane between two of the ball joints that are connected to each other by the coupling member.

* * * * *